United States Patent [19]

Mee et al.

[11] Patent Number: 4,578,635

[45] Date of Patent: Mar. 25, 1986

[54] DEVICE FOR MEASURING AND INDICATING CHANGES IN THE RESISTANCE OF A LIVING BODY

[76] Inventors: John L. Mee, 800 E. Missouri, Apartment #401, Phoenix, Ariz. 85014; Robert F. Parente, 624 Mulberry St., Plantsville, Conn. 06479

[21] Appl. No.: 570,740

[22] Filed: Jan. 16, 1984

Related U.S. Application Data

[63] Continuation-in-part of Ser. No. 224,901, Jan. 14, 1981, abandoned.

[51] Int. Cl.⁴ .......................... G01R 27/02; A61B 5/05
[52] U.S. Cl. .......................................... 324/62; 128/734
[58] Field of Search .................. 324/65 R, 62 R, 98, 324/99 R, 99 D, 131, 115, 95; 128/734

[56] References Cited

U.S. PATENT DOCUMENTS

| | | | |
|---|---|---|---|
| 2,497,961 | 2/1950 | Shaw | 324/131 |
| 3,290,589 | 12/1966 | Hubbard | 324/62 |
| 3,301,056 | 1/1967 | Blanchard et al. | 324/99 R |
| 3,302,106 | 1/1967 | Shaw | 324/62 |
| 3,714,569 | 1/1973 | Bruning, Jr. et al. | 324/131 |
| 3,873,917 | 3/1975 | Krevzer | 324/62 |
| 4,459,995 | 7/1984 | Conners | 324/65 R |

*Primary Examiner*—Reinhard J. Eisenzopf
*Assistant Examiner*—Jack B. Harvey
*Attorney, Agent, or Firm*—Cahill, Sutton & Thomas

[57] ABSTRACT

An apparatus for measuring and indicating changes in the resistance of a living body in which all changes in the resistance of the living body are displayed automatically by the apparatus. The apparatus includes a bridge network to which the resistance of the body is coupled. An amplifier is coupled to the bridge network for sensing the output voltage thereof and for providing an output signal to a meter for displaying small changes in the resistance of the body. A meter registration controller detects instances wherein the amplifier output signal is outside the range of the meter and causes a position counter to be incremented or decremented accordingly. The digital output of the position counter is converted to a non-linear analog voltage which is applied to the bridge network to automatically balance the same. The apparatus also includes a digital display for indicating the relative magnitude of the resistance of the body.

10 Claims, 11 Drawing Figures

DEVICE FOR MEASURING AND INDICATING CHANGES IN THE RESISTANCE OF A LIVING BODY

CROSS-REFERENCE TO RELATED APPLICATION

The present application is a continuation-in-part of co-pending patent application Ser. No. 224,901, filed Jan. 14, 1981 now abandoned, and assigned to the assignee of the present application, which prior application was abandoned upon the filing of the present application.

BACKGROUND OF THE INVENTION

1. Field of the Invention

The present invention relates generally to resistance measuring or indicating devices, and more particularly, to devices for indicating variations in the electrical resistance of the human body.

2. Description of the Prior Art

Devices for measuring or indicating the electrical resistance of a human body are known in the art and have found usage in psychological counselling for detecting stress and in other biofeedback applications. U.S. Pat. No. 3,290,589 discloses an electrical resistance measuring or indicating device comprising a Wheatstone bridge network having on one side thereof a first resistance arm connected to a second resistance arm, and on the other side thereof a first voltage arm connected to a second voltage arm. Between the junction of the first and second resistance arms and the junction of the first and second voltage arms there is a transistorized amplifier circuit and moving coil meter responsive to changes in balance of the bridge network, so as to indicate the resistance, or variations in resistance, of a subject such as a body connected to the network across one of the resistance arms.

In a preferred form of the aforementioned prior art device, a first variable potentiometer is associated with one of the voltage arms for controlling the range over which the device can operate to indicate variations in resistance and a second variable potentiometer is connected between the junction of the first and second resistance arms and the amplifier circuit. When the bridge network becomes unbalanced by the application of a subject thereto, balance can be restored only by the manual adjustment of the first potentiometer so that the meter will again respond to very small changes in the resistance of said subject.

Although this prior art device is useful, the need for manual adjustment of the first potentiometer means in order to balance the bridge network represents a shortcoming. When a subject applied to the bridge network, the network can become unbalanced frequently as it responds to changes in the subject's resistance. In the aforementioned prior art device, frequent manual intervention can therefore be required in order to perform adjustments of the first potentiometer to balance the bridge. This can be distracting to the person operating the device. Moreover, in view of the possibility of error which is attendant to operations requiring manual intervention, the potentiometer can be over- or under-adjusted when the operator attempts to restore balance to the bridge network. Over- or under-compensation requires further adjustment of the potentiometer to balance the device. Another shortcoming of this prior art device is related to the accuracy of its resistance indications. In the preferred embodiment of the prior art device, a range control potentiometer knob is provided to facilitate manual adjustment of the resistance range. The control knob points to positions on a linear scale calibrated in values related to subject resistance. The reading of the value on the linear scale which is pointed to by the potentiometer control knob requires operator interpretation and judgement as to the exact position of the knob on the scale. The measurements obtainable from the device are thereforesubject to a degree of human error.

It is a principal object of this invention to provide an improved device for measuring and indicating changes in resitance of a living body.

It is a specific object of the present invention to provide a device for measuring and indicating changes in resistance of a living body in which adjustment and balancing of the bridge network of the device, as it responds to resistance changes in the living body, are performed automatically by an electronic circuit instead of manually by the adjustment of a potentiometer.

It is another object of the present invention to provide a device which calculates and digitally displays the range control subject resistance value instead of requiring interpolation of a scale to discern the resistance value.

Through the fulfillment of the aforementioned objects, a final object of the invention is to provide a device for measuring and indicating changes in resistance in a living body which is easier to use and more accurate than prior art devices of the type described above.

SUMMARY OF THE INVENTION

Briefly described, and in accordance with one embodiment thereof, the present invention relates to an electrical resistance measuring or indicating device for displaying the resistance of a body and changes in resistance thereof including a bridge network having a first resistance arm extending between ground voltage and a junction node, a second resistance arm extending between the junction node and a voltage control node, and terminals for coupling the body across one of the resistance arms. An amplifier is provided for sensing a bridge output voltage and for providing a first output voltage related thereto. A meter is coupled to the amplifier and is responsive to the first output voltage for indicating changes in the resistance of the body. A meter registration controller is also provided and is responsive to the first output voltage for detecting occurrences during which the first output voltage is outside the range of values which may be displayed by the meter. Increment and decrement signals are generated when the first output voltage exceeds or falls below the range of values displayed by the meter. The meter registration controller uses the increment and decrement signals, along with clock signals provided by an associated oscillator, to increment or decrement a digital signal stored within a position counter. A non-linear digital-to-analog converter is coupled to the position counter for receiving the digital signal therefrom and for producing a non-linear analog output voltage related thereto, which non-linear voltage is impressed upon the voltage control node of the bridge network, which creates a corresponding increase in the degree of balance thereof. The aforementioned automatic readjustment process of incrementing or decrementing the position counter and correspondingly varying the analog voltage applied to the voltage control node is repeated iteratively until the bridge network is again balanced, thereby allowing the meter to again indicate changes in resistance of the body.

Another aspect of the present invention relates to the provision of a display control and digital readout for displaying a digital representation of the relative magnitude of the subject's resistance, or "tone arm display value". The display control includes a first counter responsive to the aforementioned increment and decrement signals and clock signals for storing a digital count and for selectively incrementing or decrementing the digital count each time the position counter is incremented or decremented. The first counter provides a display clock signal each time the digital count reaches a predetermined positive number, following which the digital count is reset to zero. Similarly, the first counter generates a display clock signal each time the digital count reaches a predetermined negative number, following which the first counter is reset to zero. A second counter is coupled to the first counter and is responsive to the display clock signal and to the increment and decrement signals for incrementing or decrementing a digital value stored therein corresponding to a tone arm display value. Display circuitry coupled to the output of the second counter and responsive to the digital value stored therein provides a visual display of the tone arm display value.

DETAILED DESCRIPTION OF THE PREFERRED EMBODIMENTS

Figure 1:
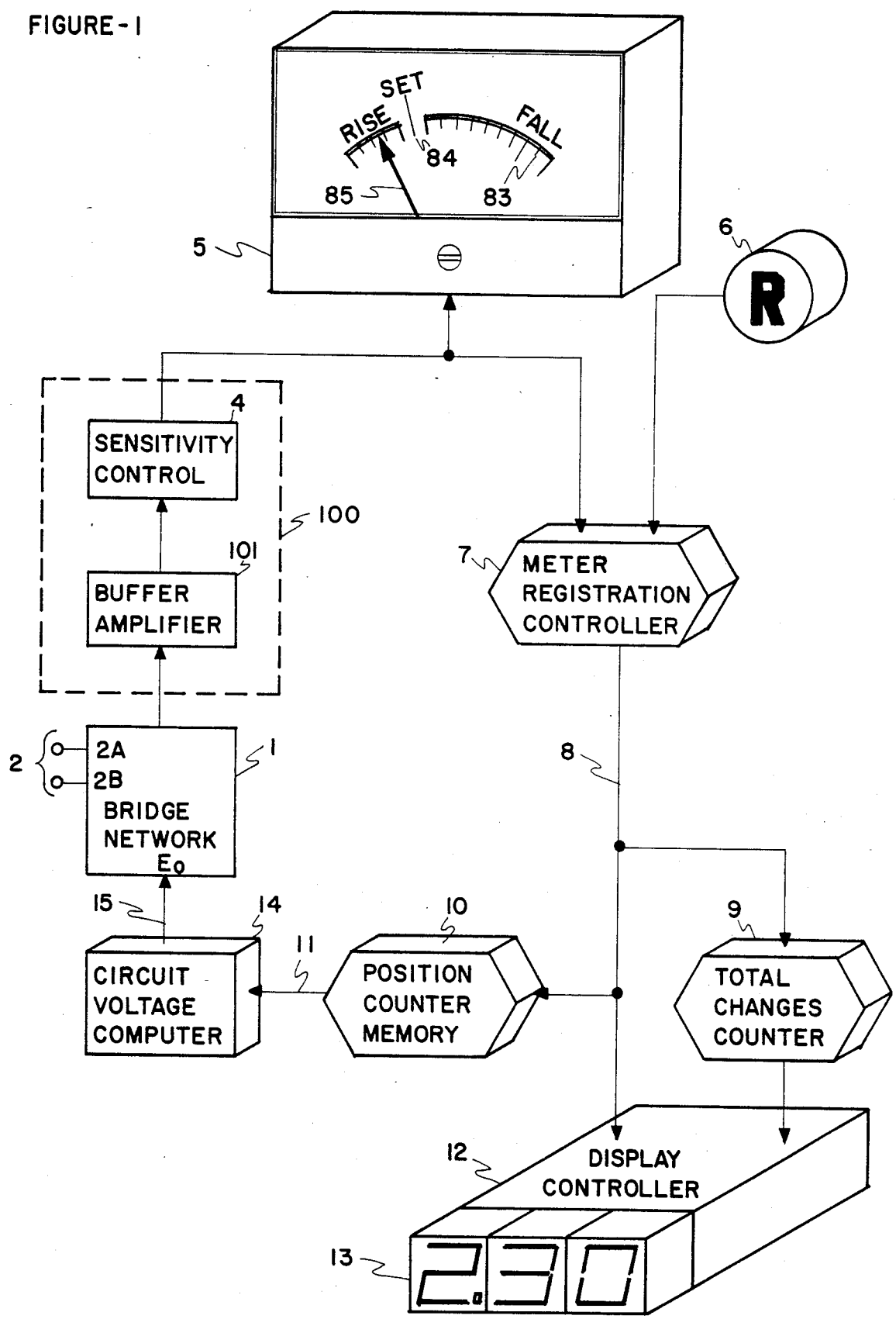
FIG. 1 is a schematic diagram illustrating the basic elements in a circuit for automatically measuring and indicating changes in resistance in a living body in accordance with the present invention.

The present invention provides an organized system of cooperating elements arranged in an electronic circuit to measure and indicate changes in the resistance of a living body, and to display all changes in the resistance of the living body automatically. For simplicity, the basic elements of the invention are illustrated in block diagram form in FIG. 1. As shown, the device comprises bridge network 1 which is typically a voltage divider bridge arrangement for the purpose of detecting small changes in resistance. Terminals 2 are provided to connect a human subject to bridge network 1 via suitable hand-held electrodes (not shown). Changes in resistance of the human subject cause bridge network 1 to become unbalanced. The bridge network produces a bridge output voltage or error voltage. In order to indicate the changes in resistance of the subject, the error voltage is applied by an amplifier 100 which includes a buffer amplifier 101 and a sensitivity control 4. The error voltage is amplified and offset by amplifier 101, as described below, and is further amplified by sensitivity control 4, which is an amplifier with its gain set by a variable control. The amplified error voltage provided by amplifier 100 is coupled to meter 5, and changes in the amplified error voltage are registered as needle deflections on meter 5 in order to display variations in the resistance of the subject.

Meter 5 has a reading range from zero uA at the extreme left of the dial to one hundred uA at the extreme right of the dial. Changes in the subject's resistance normally cause needle motion within the limits of the dial. However, large changes can cause meter needle 85 to deflect to the end of meter scale 83 at either the extreme left side (amplified error voltage corresponding to zero uA or negative) or the extreme right hand side (amplified error voltage corresponding to one hundred uA or more). Meter registration controller 7 monitors the value of the amplified error voltage for initiating an automatic readjustment process whenever this extreme imbalance occurs. Reset button 6 can also serve to instruct meter registration controller 7 to initiate the resetting process at any time by manual depression of the button. Meter registration controller 7 is coupled by a group of conductors, designated generally in FIG. 1 by conductor 8, to position counter memory 10 for transmitting thereto increment/decrement control signals. The increment/decrement control signals instruct position counter memory 10 to count up, count down or to remain unchanged. Conceptually, these control signals can be simplified to a single circuit value control signal having three possible values: +1, -1, and 0. If the device is operating within the normal limits of meter 5, and the resetting process has therefore not been initiated, the circuit value control signal will be zero since in this case no adjustments to the circuit are necessary. When the resetting process has been initiated by meter registration controller 7, the circuit value control signal will be +1 if the resetting process was initiated by meter needle 85 reaching the extreme left end of meter scale 83 (0 uA), or -1 if the resetting process was initiated by the meter needle having reached the extreme right end of meter scale 83 (100 uA).

Conductor 8 is also coupled to total changes counter 9. If the circuit value control signal has a value of -1, it increments total changes counter 9, which is a memory register provided for the purpose of accumulating total changes in the subject's resistance over a period of time, for eventual readout via display controller 12 and digital display 13.

Position counter memory 10 is a memory register which contains a digital value representation of the resistance measurement of bridge network 1 across the electrodes connected to terminals 2. The value in position counter memory 10 reflects the resistance value across terminals 2 at the most recent time the bridge network was last balanced. Bridge network 1 is considered to be when meter need 85 is at set point 84. The value in position memory counter 10 remains fixed until it is updated by the resetting process. When the control signals conducted by conductor 8 are applied to position counter memory 10, it either increments by one, decrements by one, or does not change, the digital value representation stored therein. The digital representation of bridge network 1's resistance stored in position counter memory 10 can have one value at any given moment from '0' to approximately '4100', assuming a 12-bit binary count ($2^{12}$ equals 4096). A scheme is employed whereby high numerical values correspond to high circuit resistance levels and low numerical values correspond to lower circuit resistance levels.

Conductor 8 is also coupled to display controller 12. Display controller 12 contains logic for translating the resistance changes signified by the increment and decrement control signals and clock signals into a subject resistance readout measurement, ranging in format value from '1.00' to '6.00'. Display controller 12 also contains a display driver to transmit the readout measurement to digital display 13, which may itself be comprised of three seven segment light emitting diode display or their equivalents. The readout measurement is a numerical representation of the relative magnitude of the subject's resistance (plus or minus any resistance offset indicated by the needle deflection on meter 5).

Position counter memory 10 transmits the digital representation stored thereby to circuit voltage computer 14 via a plurality of conductors collectively designated by conductor 11 in FIG. 1.

Circuit voltage computer 14 contains circuitry to generate an analog output non-linear voltage signal as a non-linear function of the digital representation provided by position counter memory 10. The analog output voltage is coupled by conductor 15 to the $E_o$ input of bridge network 1 for causing the bridge network to become balanced for each possible human subject resistance value representable by position counter memory 10. The analog output voltage signal does not have a linear correspondence with the value of the contents of position counter memory 10 because the resistance measurement characteristics required of the device are non-linear. Details of the non-linear response characteristics required of the device are discussed below in regard to FIG. 6.

If the increment and decrement control signals and clocking signals transmitted by conductor 8 are again conceptualized as a circuit value control signal, then the following example explains the circuit operation in the case of meter needle 85 reaching the extreme right side of meter 5. Meter registration controller 7 initiates the automatic resetting process to bring meter needle 85 back toward set point 84, and accordingly transmits a circuit value control signal with a value of $-1$. The stored number in position counter memory 10 will be decremented by one, and the decremented number will be input to circuit voltage computer 14. Display controller 12 will also receive the circuit value control signal and periodically update the measurement displayed by digital display 13. Upon receipt of the reduced positional digital value via conductor 11, circuit voltage computer 14 will apply a lower voltage to the $E_o$ input of bridge network 1, which in turn will lessen the degree of imbalance of the bridge network. This decrease in the degree of imbalance will begin to normalize the error voltage produced by the bridge network.

The amplified error voltage provided by amplifier 100 is continuously monitored by meter registration controller 7. If the amplified error voltage has not been corrected to the balance point, corresponding to a location for meter needle 85 at set position 84, then meter registration controller 7 will transmit a second circuit value control signal with a value of $-1$. Transmission of this signal will cause the automatic adjustment process described above to repeat itself. Usually a plurality of iterations of this process will be necessary to reset meter needle 85 to the set point. The number of such iterations required is a function of the sensitivity control setting and will be discussed in further detail below. The resetting process continues until meter registration controller 7 determines that meter needle 85 has reached set point 84 and subsequently terminates further resetting activity by transmitting a circuit value control signal with a value of zero. Signals with a zero value will continue to be transmitted by meter registration controller 7 as long as meter needle 85 is operating normally within the limits of meter 5.

When automatic resetting is again required, meter registration controller 7 will again trigger the resetting process by transmitting a circuit value control signal with a $+1$ or a $-1$ value. Resetting the analog output voltage supplied to the bridge network 1 and adjustment of digital display 13 when the meter needle reaches the extreme left side of the dial is identical in principle to the process just described for resetting the device for decreases in resistance.

Figure 2:
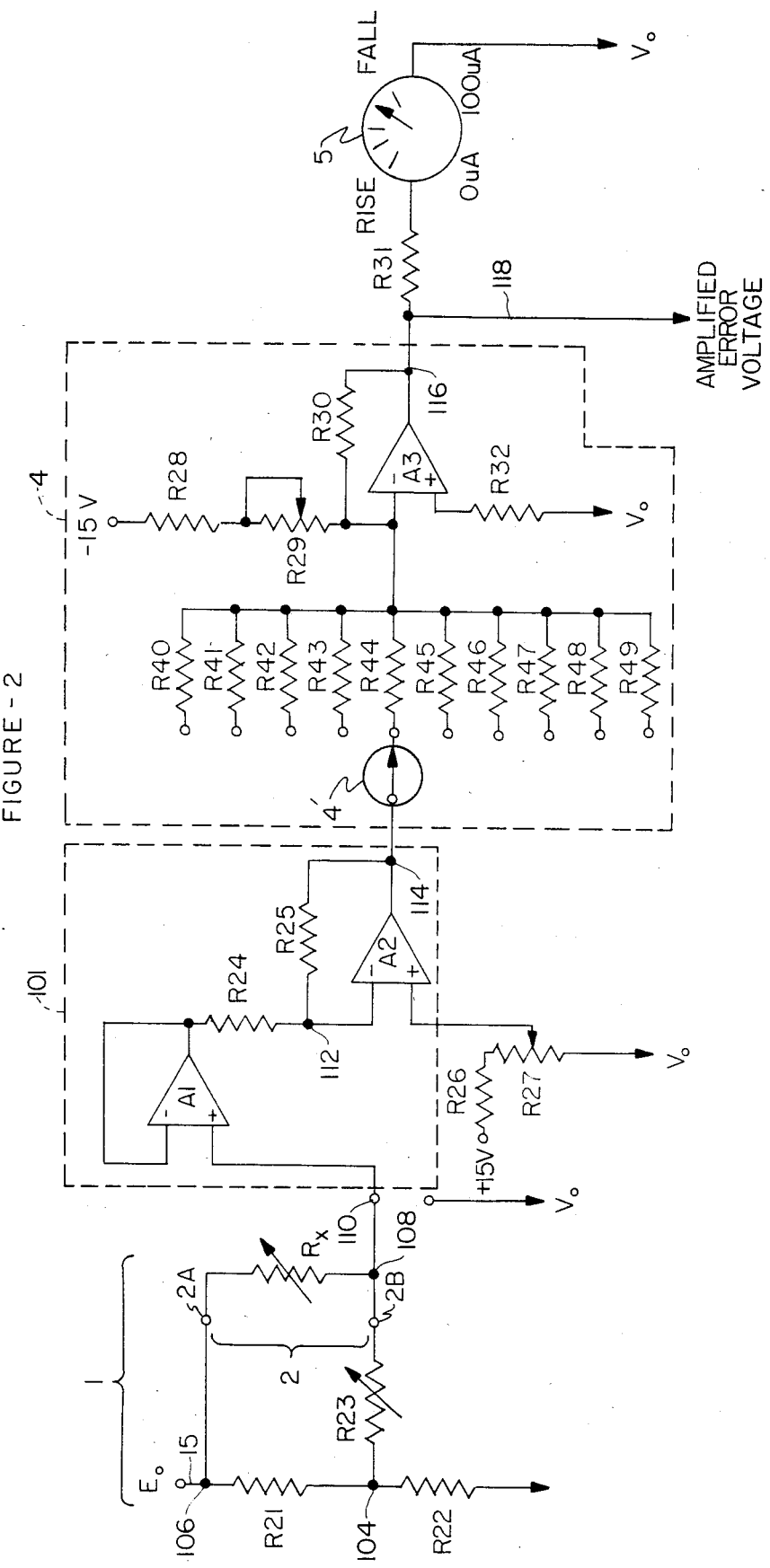
FIG. 2 is a circuit diagram of the device shown in FIG. 1 showing details of the bridge network, buffer amplifier sensitivity control, and meter.

FIG. 2 shows the details of the subject resistance variance detection bridge network 1, buffer amplifier 101, and sensitivity control circuit 4. In the embodiment illustrated, bridge network 1 is a network arranged to provide what may be termed a "voltage divider" bridge having two resistance arms constituted respectively by resistors R21 (22K) and R22 (4.56K) which form a potential divider adjusted to a ratio of 4.82:1. One end of resistor R22 is coupled to voltage commom terminal Vo which may be coupled to a source of ground potential. The second end of resistor R22 is coupled to junction node 104. One end of resistor R21 is coupled to function node 104, and the second end thereof is coupled to a voltage control node 106. As shown in FIG. 2, voltage control node 106 is coupled to conductor 15 for receiving the analog output voltage from circuit voltage computer 14 (see FIG. 1). Voltage control node 106 corresponds to the $E_o$ input of bridge network 1 shown in FIG. 1

Still referring to bridge network 1 of FIG. 2, electrode terminals 2 (2A and 2B) are provided for the connection of bridge network 1 to the body of a human subject, having a resistance represented by Rx. Terminal 2A is connected to voltage control node 106. Terminal 2B is connected through a preset 5K variable resistor R23 to junction node 104. When the device is applied to the body of a human subject, as by having the subject grip the terminal electrodes in his or her hands, the body resistance Rx shunts the resistor R21, thereby unbalancing the bridge, or causing the degree of unbalance of the bridge to change. As explained above, meter registration controller 7 (See FIG. 1) will then act to restore balance to the bridge network through correcting the analog output voltage $E_o$ if the degree of unbalance inhibits reading of the meter dial. Circuit voltage computer 14 (see FIG. 1) is calibrated to generate $E_o$ voltage values which, when applied to bridge network 1, will cause the bridge network to be balanced for any given level of subject resistance Rx. The instrument then becomes very sensitive to changes in the body resistance of the subject; a very small change of such resistance causing a relatively large change in the deflection of the meter pointer. The value of voltage $E_o$ is updated whenever a meter readjustment process is initiated by meter registration controller 7 (FIG. 1), but otherwise it is a constant voltage applied to the bridge.

Given that the voltage $E_o$ applied to bridge network 1 normally has a constant value, the instrument registers small changes in the subject resistance Rx in the following way. Bridge network 1 produces an error voltage, or bridge output voltage, at node 108 coupled to terminal 2B. When subject resistance Rx increases, the error voltage output from node 108 of bridge network 1 drops. This causes the meter needle to swing to the left (in the direction of zero error volts) towards the area of the dial marked RISE (see FIG. 1), signifying a rise in subject resistance. If the needle reaches the far end of the RISE area of the dial, meter registration controller 7 (see FIG. 1), in conjunction with position counter memory 10 and circuit voltage computer 14, will cause the value of voltage $E_o$ to be increased via the automatic resetting process. Application of this increased voltage $E_o$ to bridge network 1 will increase the error voltage to its original level and move the meter needle to the right towards the SET point. Conversely, when subject resistance Rx decreases, the error voltage at node 108 increases. The larger error voltage moves the needle of meter 5 (see FIG. 1) toward the area of the dial marked FALL, signifying a fall in subject resistance. If automatic resetting is initiate in this case, the value of voltage $E_o$ will be decreased. Application of the decreased $E_o$ voltage to bridge network 1 will decrease the error voltage at node 108 to its orginal level and move the meter needle to the left toward the SET point.

The error voltage output from bridge network 1 at node 108 is applied to an input 110 of buffer amplifier 101 which includes amplifiers A1 and A2. Amplifier A1 is a high input impedance operational amplifier. High input impedance is needed in order to keep the input resistance of the rest of the circuit high relative to the resistances within bridge network 1. If amplifier A1 did not have a high input impedance, then the value of variable resistor R23 would need to be varied as a function of the input impedance of amplifier A1 and thereby cause manufacturing problems.

Amplifier A2 of buffer amplifier 101 is a unity gain op-amp having an inverting input terminal coupled to node 112. Amplifier A2 inverts the signal applied to it by amplifier A1 via resistor R24. Resistors R24 and R25, typically 10K ohms each, establish unity gain for amplifier A2. Connection of the signal from amplifier A1 to the negative input terminal of amplifier A2 inverts the signal, i.e., a positive input signal from amplifier A1 results in a negative output signal of identical magnitude from output node 114 of amplifier A2. Resistors R26 (20K) and R27 (10K) are arranged to offset the bridge network error voltage signal by 1.700V. The reason for this is that 1.700V is the nominal, "idle" output voltage at node 108 of bridge network 1 when the bridge is fully balanced. By removing an offset voltage of 1.700V from the signal present by amplifier A2, the buffered error voltage signal output from node 114 of amplifier A2 is reduced to 0.000 V when the bridge is in a balanced condition.

In the operation of a device for measuring and indicating changes in the resistance of a human body, it is desirable to be able to adjust and control the sensitivity with which such changes are displayed on meter 5. Accordingly, sensitivity control circuit 4 is provided to serve as an operator-variable amplifier for the purpose of increasing or decreasing the amount of needle pointer deflection which a given change in the subject's resistance will produce in meter 5. Sensitivity control circuit 4 includes a control knob 4' and an operational amplifier A3. Amplifier A3 is a variable gain op-amp which increases the amplitude of the buffered offset signal output from amplifier A2 and re-inverts the phase thereof. Amplifiers A1, A2 and A3 can typically be comprised of type LM324 op-amps. The gain of amplifier A3 is set by one of resistors R40–R49. A 100K feedback resistor R30 also assists in setting the gain for amplifier A3. Resistors R40–R49 are each connected to a terminal of a ten position rotary switch operated by control knob 4'. Operator selection of a particular sensitivity position will cause the gain of amplifier A3 to be determined by the corresponding selected one of resistors R40–R49 Table 1 shows the relationship between typical values for sensitivity positions, resistance, gain of amplifier A3 and the amount of change in error voltage required to move meter needle 85 across one full dial face ($\Delta V$).

TABLE 1

| Sensitivity Scale | Resistor | Resistance | Gain | Sensitivity ($\Delta V$) |
|---|---|---|---|---|
| 1 | R40 | 5.25K | 19.05 | .525 |
| 2 | R41 | 3.65K | 27.40 | .365 |
| 3 | R42 | 2.55K | 39.22 | .255 |
| 4 | R43 | 1.75K | 57.14 | .175 |
| 6 | R44 | 1.22K | 81.97 | .122 |
| 8 | R45 | .850K | 117.65 | .085 |
| 16 | R46 | .590K | 169.49 | .059 |
| 32 | R47 | .410K | 243.90 | .041 |
| 64 | R48 | .285K | 350.88 | .0285 |
| 128 | R49 | .200K | 500.00 | .0200 |

Amplifier A3 provides an amplified error voltage signal at output node 116 thereof, which amplified error voltage signal is linearly related to the error voltage produced at node 108 of bridge network 1. The amplified error voltage is applied to moving coil meter 5 through resistor R31, which converts the amplified error voltage to a current to be measured by meter 5. Resistor R31 limits the current from amplifier A3 to meter 5. Since meter 5 registers full scale deflection at 100 uA, and since the maximum output from amplifier A3 is 10V, then resistor R31 has a value of 100K ohms (100 uA equals 10 V divided by 100K ohms.)

It is desired to have the meter needle rest at the SET position (see FIG. 1) one-third of the way across the meter dial when bridge network 1 is perfectly balanced. To achieve this, resistor R29 of amplifier A3 effectively offsets the output voltage at node 116 of amplifier A3 by a positive 3.3. volts so that a buffered voltage signal from amplifier A2 of zero volts will supply 33 uA of current to meter 5, yielding the desired deflection of the meter needle to the SET position. Resistor R28 (348K) assists in setting this offset voltage to 3.3V.

Referring again to bridge network 1 of FIG. 2, preset variable resistor R23 serves to allow manual calibration of the device when known resistance values are substituted for subject resistance Rx. At the time of manufacture, R23 is adjusted in such a way that when a 5K ohm resistor is connected between terminals 2A and 2B instead of subject resistance Rx, a balance is established with a digital readout measurement of '2.00' on display 13 (see FIG. 1) and meter needle 85 located at SET position 84 on the meter dial. The meter can be calibrated at any time thereafter by connecting a 5K ohm resistor across terminals 2A and 2B and manually adjusting R23 by means of trim control knob 80 (see FIG. 11) to bring the meter display and needle pointer to the correct registration. Resistor R32 (2.21K) coupled to the non-inverting input of amplifier A3 is provided to assist in equalizing leakage resistance between leakage current from amplifier A3 and sensitivity gain resistors R40–49, so that the output from amplifier A3 is stable and consistent.

Figure 3:
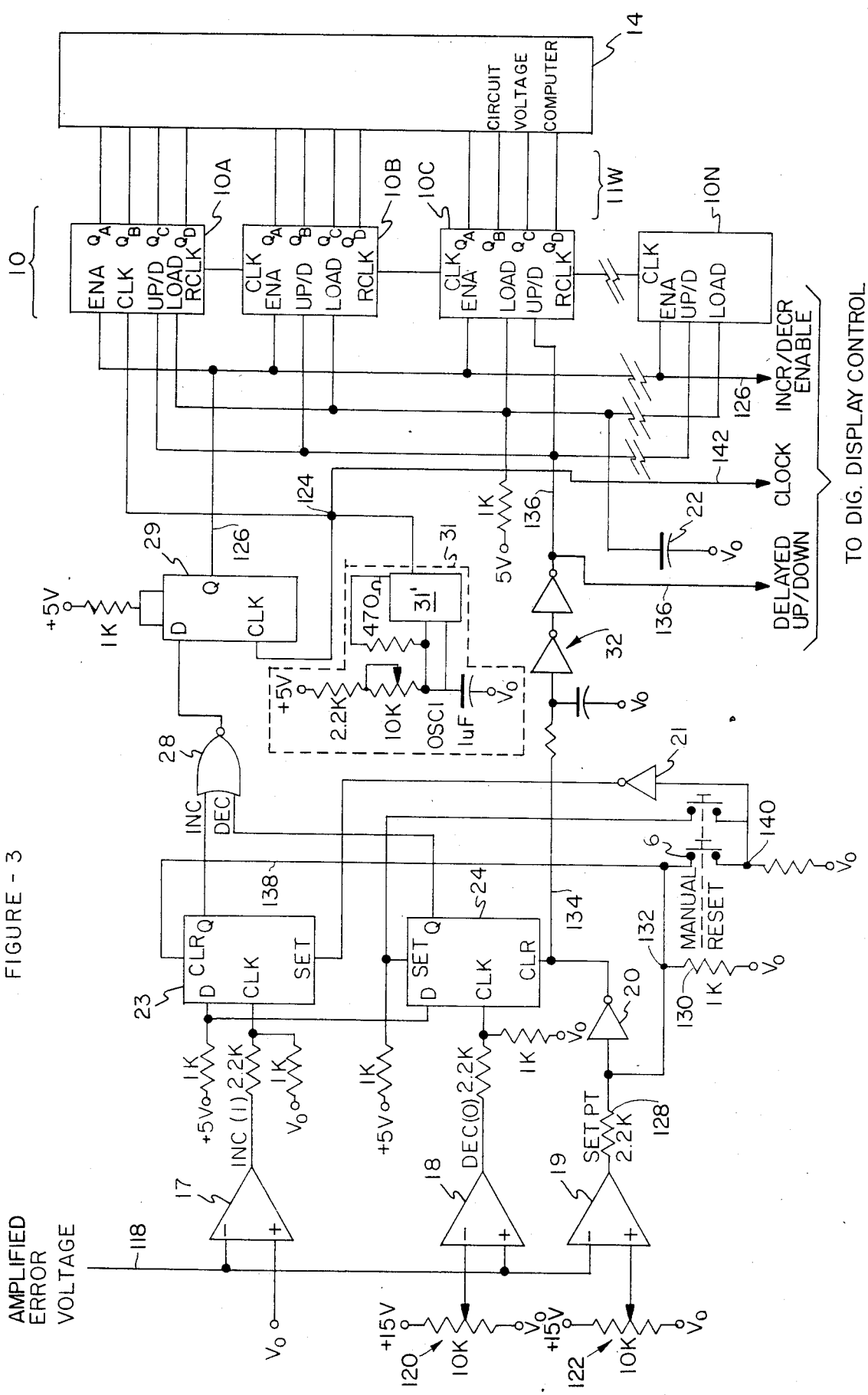
FIG. 3 is a circuit diagram of the device shown in FIG. 1 showing details of the meter registration controller and position counter memory.

Meter registration controller 7 is shown in greater detail in FIG. 3, along with position counter memory 10 and reset button 6. Referring to FIGS. 2 and 3, conductor 118 is coupled to the output node 116 of amplifier A3 for conducting the amplified error voltage provided thereto. Conductor 118 is coupled to an input terminal of each of comparators 17, 18, and 19 for applying the amplified error voltage thereto. Comparator 17 sources current from its output terminal when the error voltage has diminished to approximately 0 volts, corresponding to a meter current below 1 $\mu$A. Thus, when meter needle 85 (FIG. 1) reaches the extreme left end of the "Rise" area of the dial face of meter 5, comparator 17 will sense the correspondingly low amplified error voltage and activate an automatic circuit readjustment process. Comparator 18 performs in a similar manner when meter needle 85 reaches the extreme right end of the "Fall" area of the dial face of meter 5. Comparator 18 sources current from its output terminal to initialize the automatic circuit readjustment process when the amplified error voltage reaches +10.0 V, corresponding to 100 uA of meter current, thereby producing the fullest needle deflection to the right of the scale. The comparator threshold setting of +10.0V is controlled by a potentiometer 120 as shown in FIG. 3 to facilitate accurate adjustment of the device.

Once the circuit readjustment process has been initiated either by comparator 17 (to match increased resistance of the subject) or by comparator 18 (to match decreased resistance of the subject), the readjustment process will continue as further described below until such time as bridge network 1 becomes balanced. Bridge network 1 is considered to be balanced when the amplified error voltage produces a meter current of 33 uA, because at this point, meter needle 85 will be deflected one-third of the distance on arcuate scale 83, which corresponds to the location of set point 84 (FIG. 1.). Therefore, the objective of meter registration controller 7 is to continue the readjustment process until meter needle 85 has returned to set point 84 and no longer. Comparator 19 is provided for the purpose of terminating the automatic readjustment process at the desired point. Comparator 19 is conditioned by a potentiometer 122 to generate an up/down signal indicating whether the meter needle is above or below SET point 84, corresponding to a meter current level of 33 uA at the SET point. Activation of comparator 19 terminates the readjustment process in a manner described below.

When the instrument is operating normally and movement of meter needle 85 is within the limits of the meter dial face, no resetting is necessary, and the amplified error voltage conducted by conductor 118 varies without causing comparators 17 or 18 to be activated. Comparator 19 can be frequently switched as the movements of meter needle 85 pass back and forth over set point 84 as part of normal device operation within the limits of the dial face. When switched in these instance however, comparator 19 has no effect upon circuit operation since a resetting operation was not in progess Still referring to FIG. 3, incrementor 23 is a D-type flip-flop which functions to enable an increment operation for increasing the value of the number stored in position counter memory 10. Incrementor 23 is normally activated by comparator 17. Decrementor 24 is also a D-type flip-flop which functions to enable a decrement operation for decreasing the value of the number stored in position counter memory 10. Decrementor 24 is normally activated by comparator 18. Incrementor 23 and decrementor 24 can also be activated by manual reset button 6, described in greater detail below. Once incrementor 23 is activated, it will remain in a SET condition until cleared by operation of comparator 19. Once decrementor 24 is activated, it will likewise remain in a SET condition until cleared by operation of comparator 19.

Position counter memory 10 is shown in FIG. 3 to be comprised of memory elements 10A, 10B, 10C . . . 10N, which are typically comprised of type 74191 four-bit binary counters. Capacitor 22 (100 uf) is coupled between ground voltage Vo and the LOAD input of counter 10A-10N to initialize the binary counters with zeros when power is first applied to the device.

Enable switch 28, which may be a type 7402 NOR gate is responsive to the logic states of flip-flops 23 and 24 and is activated by the set condition of either incrementor 23 or decrementor 24. The output of enable switch 28 serves as the DATA input to a further D-type flip-flop 29. Thus, if either incrementor 23 or decrementor 24 is activated to a SET condition, then a logic "0" is clocked into flip-flop 29. The clock input CLK of flip-flop 29 is coupled to the output node 124 of an oscillator circuit 31, which includes a National Semiconductor integrated circuit type 555 timer designated by reference numeral 31'. Oscillator circuit 31 provides a continuous series of periodic clock signals. Thus, D-type flip-flop 29 is repetitively clocked by such clock signals. The output of flip-flop 29 is coupled to conductor 126, which is in turn coupled to the ENABLE input of each of the position counter memory elements 10A, 10B, 10C . . . 10N in the array. Flip-flip 29 thereby enables or disables the incrementing and decrementing of the position counter memory 10.

As mentioned above, comparator 19 is used to detect whether the amplified error voltage is above or below 3.3V, and hence, whether the meter needle is above or below the SET point 84. The output voltage developed by comparator 19 is divided across resistors 128 and 130 for providing a first up/down signal at node 132. Node 132 is coupled to the input of an inverter 20 which provides a second up/down signal that is the logical complement of the first up/down signal. The output of inverter 20 is coupled by conductor 134 to an up/down delay circuit 32. As shown in FIG. 3, delay circuit 32 includes an R-C network and a pair of wave-shaping, series-coupled inverters. The output of delay circuit 32 is coupled by conductor 136 to the UP/DOWN input terminals of counters 10A-10N for applying a delayed up/down signal thereto. The delayed up/down signal thereby instructs position counter memory 10 whether an increment operation or a decrement operation is required. The purpose of delay circuit 32 is to prevent a race condition between the up/down signal as against the enable signal applied to conductor 126 by flip-flop 29.

Output node 124 of oscillator 21 is coupled to the clock (CLK) input of counter 10A for applying clock signals thereto. If flip-flop 29 enables counter 10A, then it will be incremented or decremented by each clock signal, as determined by the status of the delayed up/down signal. The ripple clock (RCLK) output of counter 10A is coupled to the clock (CLK) input of counter 10B so that overflow or underflow in counter 10A provides a clock pulse to counter 10B. Counters 10B, 10C-10N are chained together in similar fashion. This increment/decrement process continues at the frequency of oscillator 31 as long as the activated incrementor 23 or decrementor 24 continues to provide a logic "1" to enable switch 28.

As the number contained in position counter memory 10 is increased or decreased by this process, the analog output voltage $E_o$ applied by circuit voltage computer 14 to bridge network 1 will change to reflect changes in the number stored in position counter memory 10. The numerical value in position counter memory 10 is supplied through linear digital signal wires 11W to circuit voltage computer 14, which in turn will translate each new digital positional value in memory into a new analog voltage value to be applied to bridge network 1, as explained in further detail below. Thus, the positional numeric value in position counter memory 10, from which the $E_o$ voltage is derived by circuit voltage computer 14, is incremented or decremented by oscillator 31 until the $E_o$ voltage reaches the proper level of parity with the subject's resistance; comparator 19 then clears either incrementor 23 or decrementor 24 and thus disables enable switch 28, thereby terminating the readjustment process As shown in FIG. 3, the enable signal provided by flip-flop 29, the delayed up/down signal, and the oscillator clock signal are also provided to display controller 12 (see FIGS. 4 and 5).

The specific operation of comparator 19 in controlling the circuit is as follows. Comparator 19 instructs the circuit that the device is in a decrementing condition whenever the meter needle is above set point 84 (amplified error voltage above 3.3V) by transmitting a control signal of logic "0". Conversely, comparator 19 instructs the circuit that the device is in an incrementing condition whenever the meter needle is below the set point (amplified error voltage below 3.3V) by transmitting a control signal of logic "1". The "set" and "clear" input terminals of incrementor 23 and decrementor 24 are active-low and, hence, are activated by the receipt of a logic "0" signal. Receipt of a logic "1' signal at the SET and CLR input terminals will not affect incrementor 23 or decrementor 24.

The circuit must be instructed whether the device is in an incrementing or decrementing condition at all times. Recognition of a decrementing condition will terminate an automatic incrementing resetting process. and recognition of an incrementing condition will terminate an automatic decrementing resetting process.

When the device is in a decrementing condition, comparator 19 transmits a logic "0" signal which is inverted by inverter 20 to a logic "1" signal. Inverter 20 can be a type 7404 hex inverter. The output of inverter 20 is coupled to the clear (CLR) input terminal of decrementor 24. The logic "1" signal applied to the clear terminal of decrementor 24 has no effect. Node 132 is coupled by conductor 138 directly to the clear input of incrementor 24; thus, the logic "0" signal output from comparator 19 is applied directly to the clear terminal of incrementor 23. This will terminate the automatic incrementing resetting process at the point when the device changes over from incrementing to decrementing condition (i.e., meter needle reaches set point 84).

As shown in FIG. 3, a manual reset button 6 is provided for allowing an operator to manually initiate a resetting of the $E_o$ analog voltage applied to bridge network 1. Comparator 19 serves to ensure that incrementor 23 is cleared whenever manual resetting is initiated during a decrementing condition. Depression of double pole single throw manual reset button 6 electrically couples node 132 to node 140 and electrically couples node 140 to the SET terminal of decrementor 24. If the device is in a decrementing condition when reset button 6 is depressed, then a logic "0" signal from comparator 19 is applied to the SET terminal on decrementor 24, which initiates an automatic decrementing resetting process. The logic "0" signal is also applied to the input of inverter 21, which applies a logic "1" to the SET terminal of incrementor 23 without effect.

When the device is in an incrementing condition, comparator 19 transmits a logic "1" signal which is inverted by inverter 20 to a logic "0" signal. The logic "0" signal is applied to the clear terminal of decrementor 24. This will terminate the automatic decrementing resetting process at the point when the device changes over from a decrementing to an incrementing condition (i.e., meter needle reaches set point). It will also ensure that decrementor 24 is cleared whenever manual resetting is initiated during an incrementing condition. The logic "1" signal provided by the output of comparator 19 is also applied directly to the clear terminal of incrementor 23 without effect. Depression of manual reset switch 6 whenever the device is in an incrementing condition applies the logic "1" signal from comparator 19 to the SET terminal on decrementor 24, without effect. The logic "1" signal is also applied to the input of inverter 21, which applies a logic "0" signal to the SET terminal on incrementor 23, thereby initiating an automatic incrementing resetting process.

As mentioned above, comparator 19, inverter 20, and delay circuit 32 generate a delayed up/down signal which is applied to position counter memory 10. A logic "0" physical value for the delayed up/down signal indicates that an incremental count is required while a logical "1" physical value indicates a count down.

Figure 4:
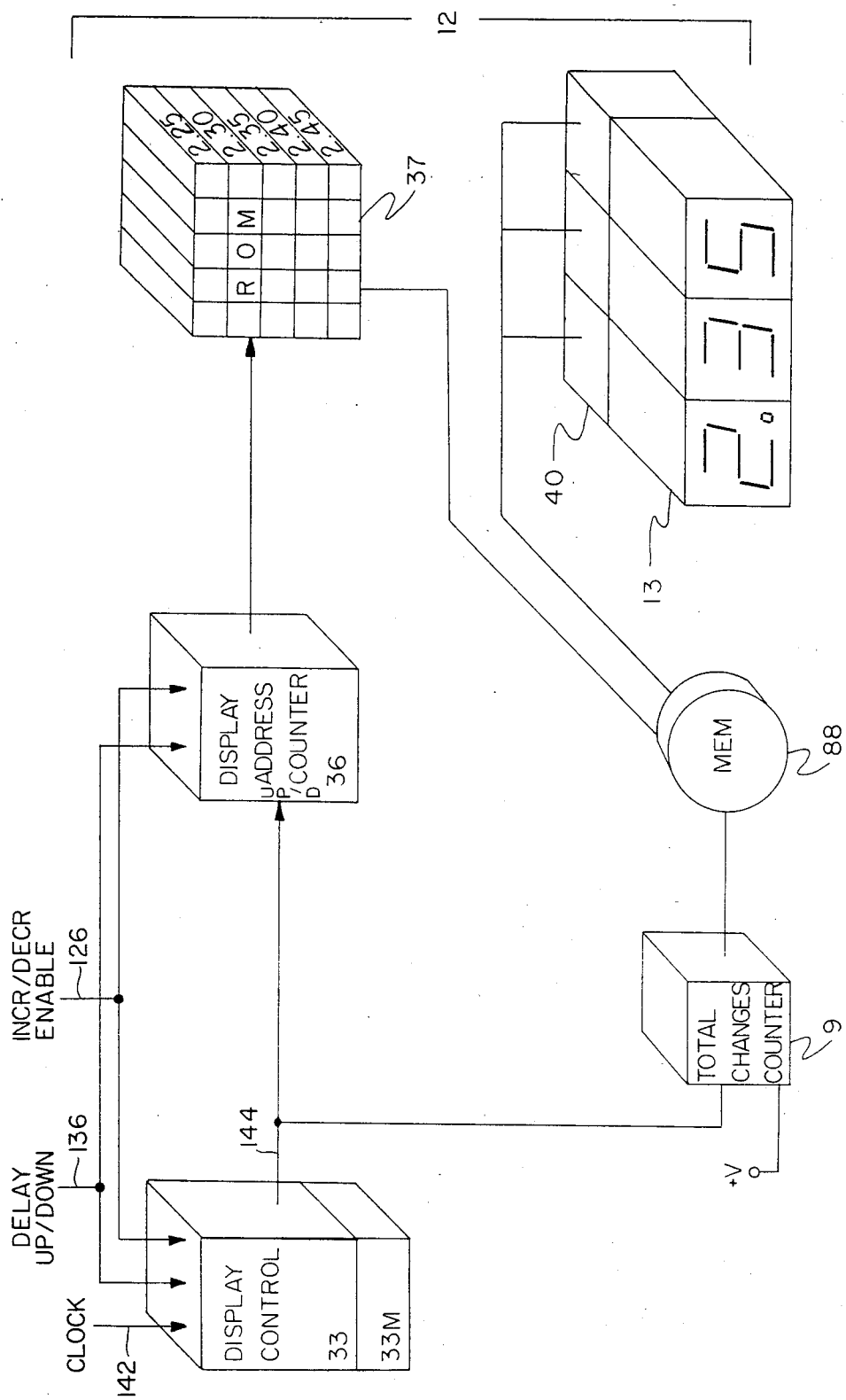
FIG. 4 is a circuit diagram of the device shown in FIG. 1 showing details of a first embodiment of the display controller and digital display using a read-only memory.

FIG. 4 shows an embodiment of the logic circuitry for producing subject resistance measurement digital readouts, hereinafter called tone arm display value readouts, which includes display controller 12 and digital display 13. Referring to FIG. 4, the increment/decrement enable signal, delayed up/down signal, and oscillator clock signals discussed above in regard to FIG. 3 are also applied to display control 33 via conductors 126, 136, and 142, respectively. Display control 33 contains intermediate memory 33M in the form of an eight-bit binary counter suitable for representing binary values ranging from "−40" to "+40". Display control 33 increments intermediate memory 33M by +1 each time position counter memory 10 is incremented. Display control 33 decrements intermediate memory 33M by −1 each time position counter memory 10 is decremented. The purpose of display control 33 is to indicate when a count of positive "41" or negative "41" is reached. When the absolute value in intermediate memory 33M reaches "41", display control 33 clears the eight-bit binary counter and transmits a clock pulse via conductor 144 to the clock input of display address counter 36. The increment/decrement enable signal and delayed up/down signal are also coupled to display address counter 36. Upon receipt of a clock pulse via conductor 144, the display address value stored by display address counter 36 is incremented or decremented as determined by the status of the delayed up/down signal.

The reason display address counter 36 is modified whenever display control 33 reaches a count of positive or negative "41" is as follows. If position counter memory 10 is formed by three four-bit binary counters, then it may store $2^{12}$, or 4096, unique binary values ranging from "0" to "4095". It is desired to display resistance in tone arm display values in increments of 0.10 as follows: 1.00, 1.05, 1.10, 1.15 . . . 5.90, 5.95, 6.00. This selected number sequence from 1.00 to 6.00 is comprised of one hundred possible tone arm display numbers. If there are 4096, or roughly 4100 possible values in position counter memory 10 and one hundred possible tone arm display values, then there will be a unique tone arm display number for every 41 values in position counter memory 10, as shown in Table 2 below.

TABLE 2

| Position Counter Memory 10 Value | Tone Arm Display Value |
| --- | --- |
| 0–40 | 1.00 |
| 41–81 | 1.05 |
| 82–122 | 1.10 |
| . | . |
| . | . |
| . | . |
| 4059–4099 | 5.95 |
| 4100–4140 | 6.00 |

The choice of 4100 (actually 4095) as the maximum value for position counter memory 10 is the preferred value, although in actual volume production of the device a different maximum value could be used. Such a change would affect the above relationships and the threshold of display control 33. For example, if the maximum value were 4800 instead of 4100, then display control 33 would have a roll over value of 48 instead of 41. Alternatively, the maximum position counter memory value could be 6000 with a minimum value of 1000 and a roll over value of 50.

When modified under the control of display control 33 as explained above, display address counter 36 contains a number corresponding to the location of the number in the sequence of one hundred tone arm display number 1.00, 1.05, 1.10 . . . 5.95, 6.00 which corresponds to the value present in position counter memory 10. The value in display address counter 36, which is a number from 1 to 100, is then applied as a readout address to read-only memory 37, which fetches the corresponding number from a stored sequence of one hundred tone arm display numbers in the memory. The stored number is output from read-only memory 37 to display driver 40, which decodes the number signal and drives seven segment LED display 13 to display the number in a manner well known in the art.

FIG. 4 also shows total changes counter 9. Conductor 144 couples the display clock signal provided by display control 33 to a clock input of total changes counter 9. Thus, upon receipt of a display clock signal from display control 33, the value in total changes counter 9 is incremented irrespective of whether display address counter is incremented or decremented. During the time that an operator depresses and temporarily holds down spring contact memory display button 88, the normal path from read-only memory 37 to display drive 40 is shunted to allow momentary display of the contents of total changes counter 9 on seven segment display panel 13. Total changes counter 9 utilizes a volatile semiconductor memory to allow the memory to be cleared by turning the instrument off.

Figure 5:
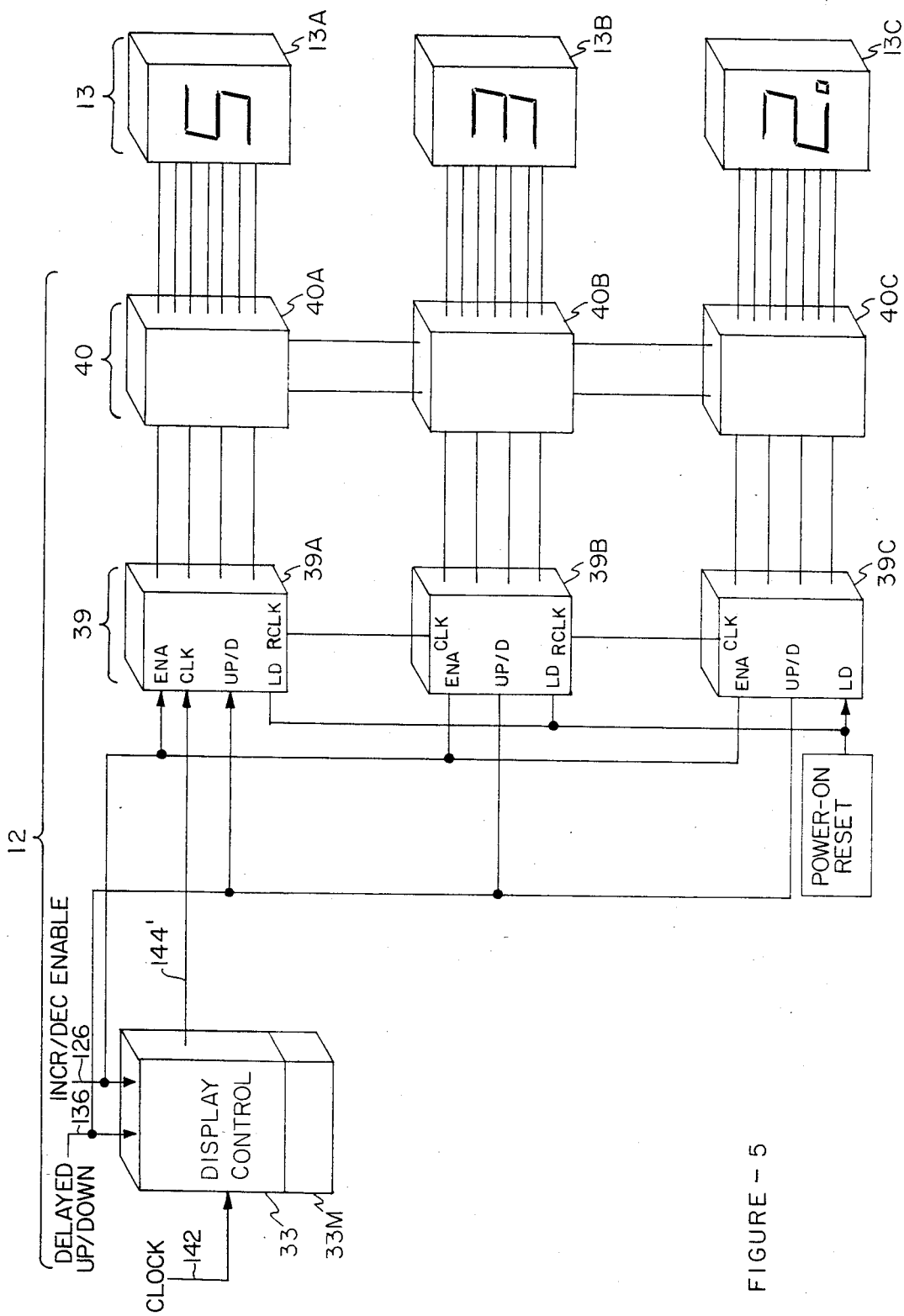
FIG. 5 is a circuit diagram of the device shown in FIG. 1 showing details of a second embodiment of the display controller and digital display using digital counters.

FIG. 5 illustrates a lower cost, and hence, preferred embodiment of the logic circuitry for producing digital tone arm display value readouts, including display controller 12 and digital display 13. The increment/decrement enable signal, delayed up/down signal, and clock signals, which drive position counter memory 10 in FIG. 3, are also applied to display control 33 as shown in FIG. 5. Display control 33 functions in the manner described above for FIG. 4 to produce a display clock signal when a binary count of positive or negative "41" is reached. The display clock signal is applied via conductor 144' to the clock input of display memory 39, which is comprised of display memory counters 39A (hundredths), 39B (tenths) and 39C (units). Display memory 39 is preset loaded with a value of "1.00" by means of a power-on preset circuit (e.g., capacitor to ground). Display memory counter 39A (hundredths) is arranged to provide values of only "0" or "5". Thus, successive increments to the preset value of 1.00 in display memory 39 would create the desired tone arm display values of 1.00, 1.05, 1.15 . . . 5.95, 6.00. As explained earlier, the threshold value of display control 33 is set at a number such as '41' to provide for 100 increments over the full range of resistance measurement of the device to produce the desired sequence of tone arm display values.

As shown in FIG. 5, conductors 126 and 136 are also coupled to the enable and up/down control input terminals, respectively, of display counters 39A, 39B, and 39C for providing the increment/decrement enable and delayed up/down signals thereto. Memory counters 39A, 39B, and 39C may be formed by type 74190 BCD counters and are incremented or decremented to reflect changes in subject resistance. The output terminals of memory counter 39 are applied to display driver 40, which is comprised of type 7447A BCD to seven segment converters 40A, 40B, and 40C. Output from these converters is applied to seven segment LED display units 13A, 13B, and 13C to provide continuous visual readout of the tone arm display value. Although not repeated here, the connections for optional total changes counter 9 between display control 33 and display driver 40 are the same here as those specified for the circuit in FIG. 4. However, memory display button 88 would be connected to shunt display memory 39 in FIG. 5, instead of read-only memory 37 as in FIG. 4.

As mentioned above, variable resistor R23 in bridge network 1 is provided for calibrating the device. Such calibration is always performed with control knob 4' of sensitivity control circuit 4 (see FIG. 2) selecting maximum gain, hence, maximum sensitivity. Position counter memory 10 is calibrated in a fixed manner to operate as if the device were set at maximum sensitivity at all times, independently from the actual setting of sensitivity control knob 4'. As stated earlier, the number of iterations of incrementing or decrementing the value in position counter memory 10 required to reset the meter needle to the set point is a function of the sensitivity setting. This is because the maximum value of position counter memory 10 is calibrated to the meter resetting accuracy which is required at the maximum sensitivity setting. To be able to reset the needle to within ±3% of the "set" position at maximum sensitivity, a reset stepping granularity of 1/4100th of the device's total resitance measuring range is required (hence, the memory range of 1–4100). Since the meter resetting calibration is fixed to this finest granularity of change, there will be more circuit iterations required to reset the needle at lower sensitivities than at higher ones. However, this greater amount of counting per reset at lower sensitivities is masked from the operator by the high speed of the electronic circuitry.

In the construction of a self-adjusting apparatus for automatically measuring and indicating changes in resistance of a living body, it is desirable to have the scale of resistance measurement, hereinafter referred to as the tone arm display scale, arranged to correspond with the analog output voltage $E_o$. Specific values used in the prototype model for tone arm display scale value, voltage applied to the bridge ($E_o$), and subject resistance ($R_x$) are shown in Table 3 below.

TABLE 3

| Tone Arm | Voltage ($E_o$) | Subject Res. ($R_x$) |
| --- | --- | --- |
| 1.00 | 1.95 V | 1.23K ohms |
| 1.25 | 2.09 | 1.86 |
| 1.50 | 2.24 | 2.63 |
| 1.75 | 2.38 | 3.73 |
| 2.00 | 2.53 | 5.00 |
| 2.25 | 2.67 | 6.53 |
| 2.50 | 2.90 | 8.25 |
| 2.75 | 3.20 | 10.25 |
| 3.00 | 3.48 | 12.50 |
| 3.25 | 3.79 | 15.80 |
| 3.50 | 4.20 | 20.00 |
| 3.75 | 4.64 | 24.20 |
| 4.00 | 5.06 | 30.10 |
| 4.25 | 5.49 | 38.00 |
| 4.50 | 5.90 | 48.30 |
| 4.75 | 6.37 | 62.30 |
| 5.00 | 7.06 | 89.20 |
| 5.25 | 7.80 | 128.20 |
| 5.50 | 8.54 | 208.0 |
| 5.75 | 9.28 | 470.0 |
| 6.00 | 9.98 | 1 Meg. |

Figure 6:
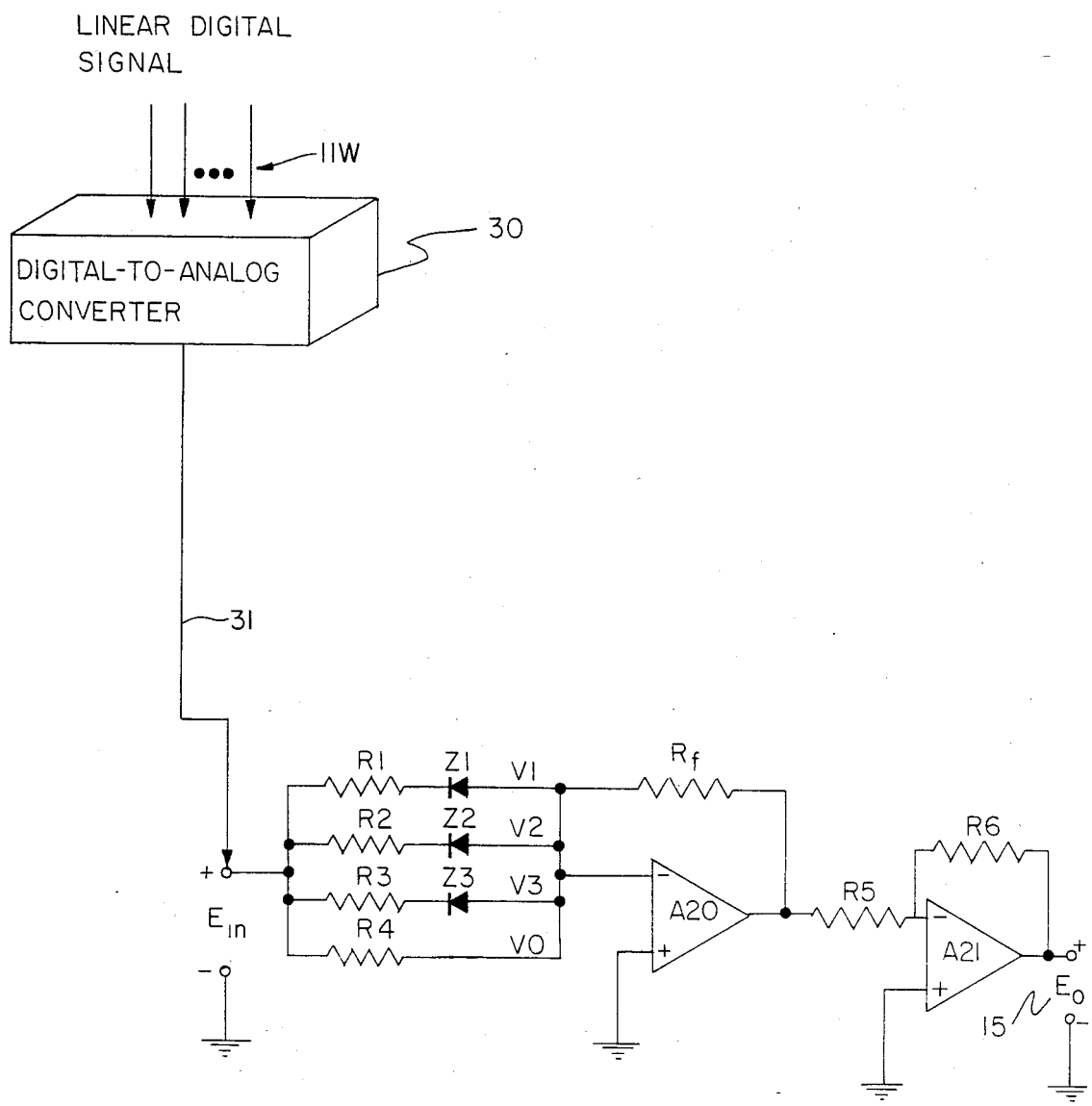
FIG. 6 illustrates a first embodiment of the circuit voltage computer shown in FIGS. 1 and 3, and in which a zener diode and resistor network non-linear voltage generation technique is used.

FIG. 6 is a circuit diagram which illustrates in detail one version of circuit voltage computer 14 mentioned earlier in regard to FIGS. 1 and 3. Circuit voltage computer 14 is one of the combination of components used to produce the desired correspondence between analog output voltage $E_o$ values, subject resistance, and tone arm display scale values as indicated in Table 3 above. Referring to FIGS. 3 and 6, wires 11W are coupled from position counter memory 10 to a digital analog converter 20 for providing thereto a digital signal representative of subject resistance. Digital to analog converter 30 transforms the input digital signal provided by wires 11W into a voltage signal linearly related to the input digital signal by means well known in the art, such as frequency to voltage conversion. The linear voltage signal developed by D-to-A converter 30 ranges from 1.000 to 6.000 volts. The value of the linear voltage signal (1.000 V–6.000 V) corresponds to the tone arm display scale value (1.00–6.00), however it has a much finer degree of resolution. Conducter 31 couples the output terminal of D-to-A converter 30 to a resistor network circuit at the point labelled $E_{in}$ in FIG. 6. The purpose of the circuit shown in Fig. 6 is to generate a non-linear analog output voltage $E_o$ at the point labelled $E_o$ in FIG. 6 which will approximate the circuit voltage values shown in Table 3 above for any given value of the input signal $E_{in}$. As mentioned above, the voltage $E_o$ is then applied by conductor 15 to voltage control node 106 of bridge network 1 (see FIG. 2).

An ideal approach for generating these values would be through the use of a singular transistor, such as a field effect transistor, which developed non-linear resistance from linear voltage input in a manner that corresponded to the analog output voltages shown in Table 3 above. However, since FETs having comparable response characteristics are not presently commercially available, another approach was used. Specifically, the desired curve was approximated through a plurality of straight line segments. Eight segments produced the best fit to the curve, but for the sake of simplicity, four segments are used in the description which follows.

The slope of each line segment can be determined, together with the location of the points on the curve at which segments intersect and a changeover occurs from one line segment approximation to another (i.e., break points). Sample break points and line segment slopes used in the prototype model were as shown in Table 4 below:

TABLE 4

| Range | Slope |
| --- | --- |
| 1.00 V – $E_{in}$ – 2.30 V | .055 |
| 2.30 V – $E_{in}$ – 3.20 V | 1.06 |
| 3.20 V – $E_{in}$ – 4.80 V | 1.65 |
| 4.80 V – $E_{in}$ – 6.00 V | 2.97 |

Thus, from a linear voltage input signal representing tone arm display scale value, the circuit shown in FIG. 6 will produce a desired output voltage corresponding to the non-linear response curve C by means of a plurality of discrete linear voltage responses arranged to resemble the characteristics of the desired response curve by using straight line segment approximations of the curve. Specific operation of the circuit is as follows:

Resistors Rf, R1, R2, R3 and R4 are selected to have values which will generate the slopes of the shown in Table 4 when the resistors are arranged in the following combinations as shown in Table 5 below:

TABLE 5

| Line Segment | Break Point | Resistor Combinations | Slope Value |
| --- | --- | --- | --- |
| S0 | V0=0.0 V | $S_0 = \dfrac{Rf}{R4}$ | 0.55 |
| S1 | V1=2.3 V | $S_1 = \dfrac{Rf}{R4} = \dfrac{Rf}{R1}$ | 1.06 |
| S2 | V2=3.2 V | $S_2 = \dfrac{R4}{R4} = \dfrac{Rf}{R1} + \dfrac{Rf}{R2}$ | 1.65 |
| S3 | V3=4.8 V | $S_3 = \dfrac{Rf}{R4} + \dfrac{Rf}{R1} + \dfrac{Rf}{R2} + \dfrac{Rf}{R3}$ | 2.97 | where S equals Slope of the line segment.

Zener diodes Z1, Z2 and Z3 would be selected with threshold values corresponding to the break points established for V1, V2 and V3. In the case of this example, Z1 would activate at 2.3 volts, Z2 at 3.2 V and Z3 at 4.8 V.

Resistors Rf/R4 would determine the initial slope at low voltages. As $E_{in}$ increased and reaches the value of V1, the Z1 zener diode would conduct, bringing resistor R1 into the circuit. With the value of R1 chosen to match the appropriate slope, the slope would then become Rf/R4+Rf/R1. When $E_{in}$ reaches the value of V2, the Z2 zener diode conducts, bringing resistor R2 into the circuit, and so on for the remainder of the break points. As $E_{in}$ decreases, the zener diodes turn off, and resistors R3, R2 and R1 are deleted from the slope-generating circuit one by one, thereby maintaining the proper slope across all areas of the range covered by the device.

The purpose of amplifier A20 is to amplify whatever slope signal it receives from the resistor/zener diode network just described. Both amplifiers A20 and A21 may typically be comprised of operational amplifiers (opamps). Since input from the resistor/zener diode network enters amplifier A20 at its negative terminal, and since the non-inverting terminal of amplifier A20 is grounded, the output from amplifier A20 is a negative voltage. Amplifier A21 is a unity gain inverter used to restore the negative voltage from amplifier A20 into a positive voltage. This is achieved through the use of 10K resistors R5 and R6 in conjunction with the input connection to the negative terminal of amplifier A21, resulting in a gain of $-1$. Thus, the output signal at $E_o$ is an amplified, positive slope signal corresoonding to the proper line segment approximation indicated in Table 4 above for all regions of the device's operating range.

Figure 7:
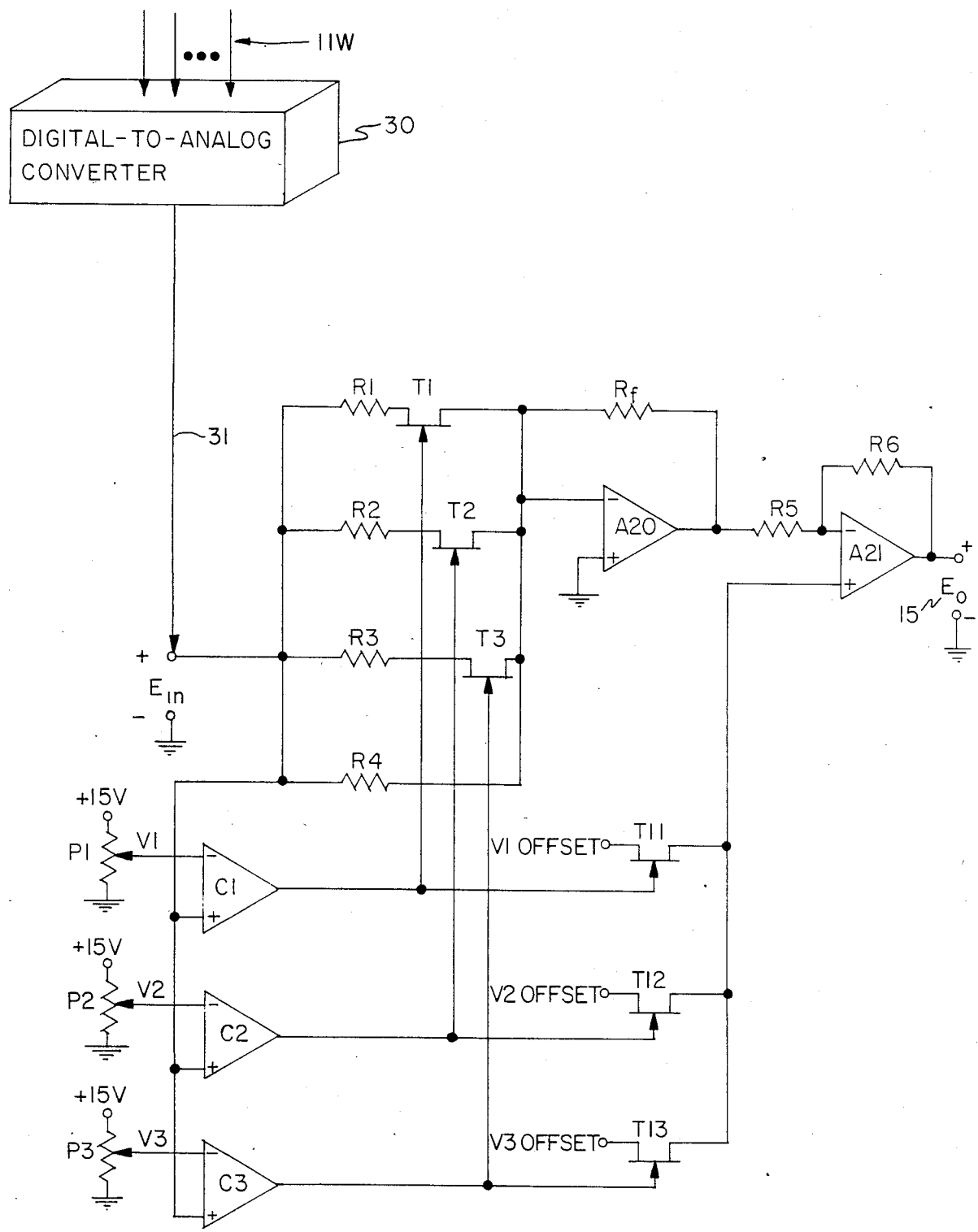
FIG. 7 illustrates a second embodiment of the circuit voltage computer, in which the resistor network uses field effect transistors in place of zener diodes.

Although the circuit just described in FIG. 6 will work and has the advantages of simplicity and a small number of components, the values of V1, V2 and V3 shown in the example are not typical zener diode breakdown voltage values. In addition, the repeatability of the exact threshold values from one zener diode to the next could be low, which in turn would tend to create device manufacturing problems in a mass production environment. Accordingly, FIG. 7 depicts a circuit which will accomplish the same function using a similar selectively-activated resistor network, but which does not utilize zener diodes.

In this circuit, as in FIG. 6, digital to analog converter 30 converts the digital signal provided by wires 11W into a linear analog voltage signal and applies the signal to the terminal labelled $E_{in}$. An arrangement of comparators C1, C2 and C3 and field effect transistors T1, T2 and T3 is used to perform the current switching function accomplished by zener diodes Z1, Z2 and Z3 in the circuit shown in FIG. 6. The comparators and transistors switch current into a resistor network comprised of Rf, R1, R2, R3, and R4. This resistor network is identical to the one appearing in FIG. 6 and functionsin the same way to provide an output voltage at the point $E_o$ which approximates the characteristics shown in Table 4. The manner in which the arrangement of comparators and transistors performs the switching of current into the resistor network is as follows.

The values of the break points V1, V2 and V3 are selected by adjustment of potentiometers P1, P2 and P3. Repeatability of break point values established with potentiometers is very good from one device to the next. When the value of the input voltage $E_{in}$ reaches the threshold of the break point voltage value V1 established by potentiometer P1, comparator C1 conducts current which is directed to the gate of transistor T1, thereby activating transistor T1. Transistors T1, T2 and T3 are field effect transistors which act as switches. When transistors T1, T2 and T3 are not receiving input current, they remain in an "off" state with an extremely high resistance so that resistors R1, R2 and R3 are kept out of the circuit. In this particular case the slope value is set by Rf/R4. When transistor T1 is activated by comparator C1, it conducts current through resistor R1, thereby bringing R1 into the circuit and changing the slope equation to Rf/R4+Rf/R1. As the value of $E_{in}$ increases up to the break point values of V2 and V3, comparators C2 and C3 activate transistors T2 and T3 to bring resistors R2 and R3 into the circuit in a similar manner. As the value of $E_{in}$ decreases from V3 down to V0, comparators C3, C2 and C1 will deactivate transistors T3, T2 and T1 and remove resistors R3, R2 and R1 from the circuit at the appropriate values of $E_{in}$ to maintain an output voltage response at $E_o$ which matches the characteristics of Table 4 for all values of $E_{in}$.

Resistors Rf, R5 and R6 and amplifiers A20 and A21 have the same functions as described in FIG. 6. Offset transistors T11, T12 and T13 are activated by comparators C1, C2 anc C3 respectively. The purpose of these transistors is to offset any overcompensation made by the circuit, in order to ensure that a smooth response slope is maintained over the whole operating range of the device.

Figure 8:
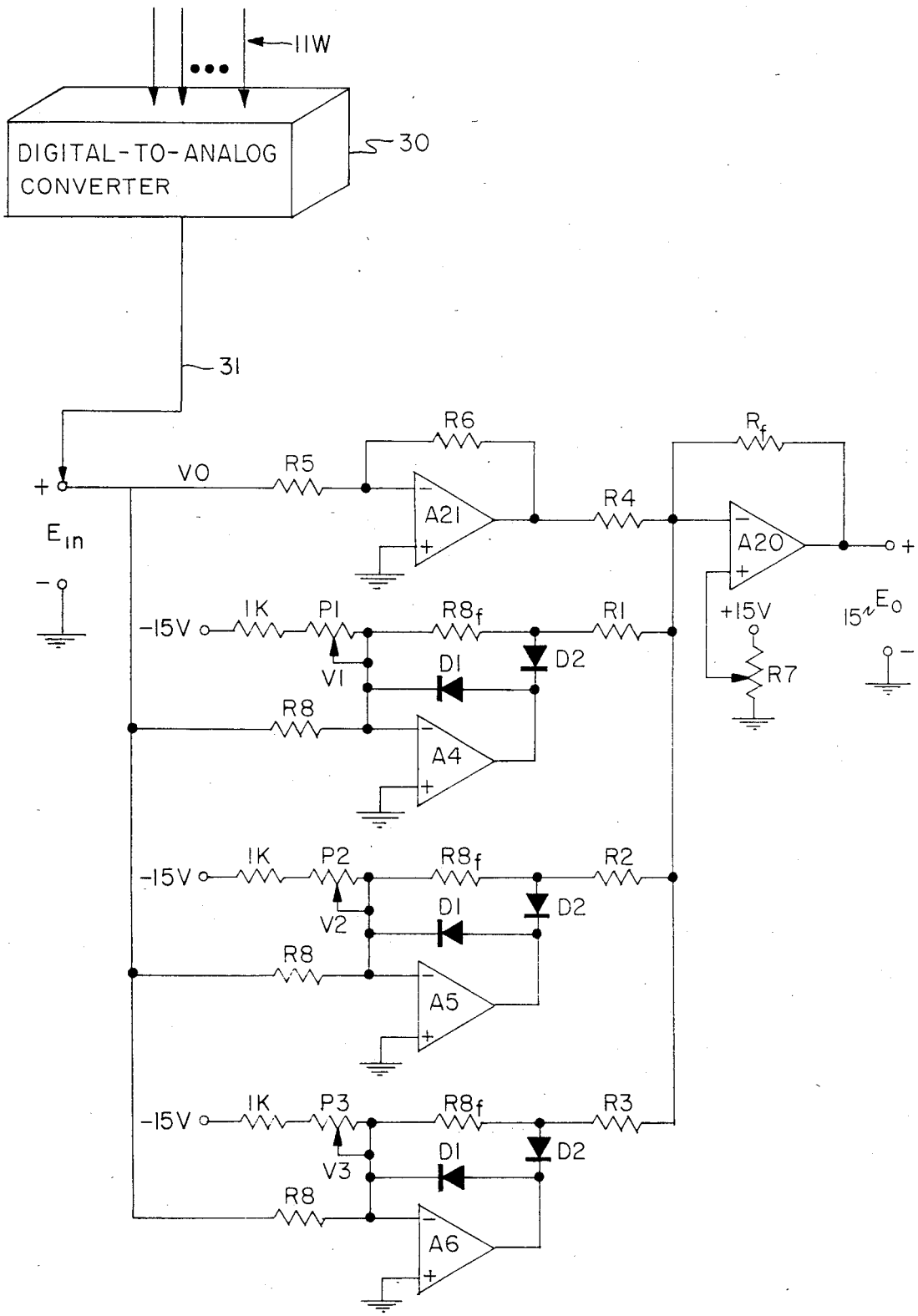
FIG. 8 illustrates a third embodiment of the circuit voltage computer, in which the resistor network uses amplifiers and diodes to generate a non-linear voltage.

In the construction of a self-adjusting apparatus for automatically measuring and indicating changes in resistance of a living body, it is desirable to achieve the lowest possible number of circuit components and least cost. FIG. 8 is a circuit diagram which illustrates in detail a highly repeatable, low cost, and preferred embodiment of the logic used to produce the desired correspondence between actual analog output voltage $E_o$ values and tone arm display scale measurement values. Specific operation of this low cost circuit is as follows:

As in FIGS. 6 and 7, digital-to-analog converter 30 converts the digital signal provided by wires 11W into a linear voltage signal and applies it via conductor 31 to the terminal labelled $E_{in}$. In this circuit, amplifiers A4, A5 and A6 switch current into a resistor network comprised of resistors Rf, R1, R2, R3 and R4. This resistor network is identical to the one appearing in FIGS. 6 and 7 and functions with amplifier A20 in the same way to provide an output voltage at the point labelled $E_o$. The values of the break points V1, V2 and V3 are selected by adjustment of potentiometers P1, P2 and P3.

The following discussion considers amplifier A4 as an example of this circuit's operation. Input voltage $E_{in}$ is applied to amplifer A4 through 1K resistor R8. Assuming that the gain of amplifier A4 is very large, then the voltage at the negative input terminal is the same as the voltage at the positive terminal (or virtual ground). When the input voltage $E_{in}$ is less than the value of the first break point V1, resistors R1, R2 and R3 must be kept out of the slope/gain summing sequence to allow resistor R4 alone to determine the slope to be used for $E_{in}$ voltages in the range between V0 and V1. Referring specifically for example to resistor R1, all current through resistor R1 must be zero until $E_{in}$ exceeds the value of V1. Potentiometer P1 has the capacity to sink the full current load at the break point V1, which yields zero volts through R1 at exactly the break point voltage. However, negative currents arising from the difference between the values of input voltage $E_{in}$ below the break point voltage V1 and the capacity of the potentiometer P1 to sink the full current load of the break point must be prevented, in order to ensure that zero volts are supplied to resistor R1 whenever the break point V1 is not exceeded. To accomplish this, amplifier A4 supplies the extra current differential needed by the current sink P1 via diode D1. Since the opamp output is positive in this case, it can only travel through diode D1.

When $E_{in}$ exceeds the value of the break point voltage V1, the excess current above the break point value cannot be absorbed by the sink P1, and forms a surplus. For example, if V1 is 2.3 V and $E_{in}$ is 3.0 V, R8f has to conduct 0.7 mA to keep the inverting input terminal of amplifier A4 at 0 volts. The path of the current is through feedback resistor R8f and diode D2 and into the output terminal of amplifier A4. Since the voltage at the output of amplifier A4 is negative, D1 is reverse biased, thereby preventing current from flowing through diode D1. By letting R8f=R8=1K, unity gain is established and the voltage across feedback resistor R8f is −0.7 V. Break point V1 is now "active". The excess input voltage above the break point voltage V1 (0.7 V in the case of the example) is converted to a corresponding current by 1K ohm resistor R8 and conducted across feedback resistor R8f; the larger the current conduct by R8f, the greater the voltage dropped thereacross, and hence, the more negative the voltage output from amplifier A4. As the output voltage drops, resistor R1 sinks more and more current from the inverting input of summing amplifier A20. Although this current is negative, it is subsequently reinverted into a positive value at the output of amplifier of A20. This is accomplished via the connection of resistor R1 to the negative input terminal of amplifier A20. The diode voltage drop of D2 is insignificant because R1 is connected to the anode of D2, so any variations in the forward voltage drop of diode D2 as a function of temperature or current have no effect.

Amplifiers A5 and A6 function with potentiometers P2 and P3 in a similar manner to sink zero currents through resistors R2 and R3 when the value of $E_{in}$ is less than the break point voltage values V2 and V3. When $E_{in}$ exceeds the voltage values of V2 and V3, resistors R2 and R3 sink current from the inverting input terminal of amplifier A20 in a similar manner of operation as discussed for amplifier A4 and resistor R1.

All input voltages $E_{in}$, whether above or below the values of the break point voltages V1, V2 and V3, are monitored by unity gain inverter amplifier A21, which functions as described in FIG. 6. However in this case, amplifier A21 converts a positive input voltage $E_{in}$ into a negative output voltage of equal magnitude, which in turn causes a negative current to flow through slope gain resistor R4. This is done because the currents conducted by the other slope gain resistors in the network, R1, R2 and R3, will also be negative. By making the voltage across R4 negative as well, the connection of the resistor network to the negative input terminal of slope amplifier A20 can allow the slope amplifier to also reinvert the sign of the voltage, so that the output signal at $E_o$ is an amplified, positive slope signal corresponding to the proper line segment approximation shown in Table 4 for all areas of the device's operating range.

Resistor R7 (10K) provides an offset voltage to calibrate the circuit. The lowest value of $E_{in}$ is 1 V. The gain slope set by resistor R4 is 0.55. The corresponding output is 0.55 V. The lowest value required for $E_o$ is 1.95 V, as shown in Table 3 above. A 1.40 V offset voltage provided through resistor R7 added to the 0.55 V voltage calibrates the circuit to the desired starting point (1.95 V) for its response curve. The offset voltage is a constant which would be set at the time of manufacture.

Figure 9:
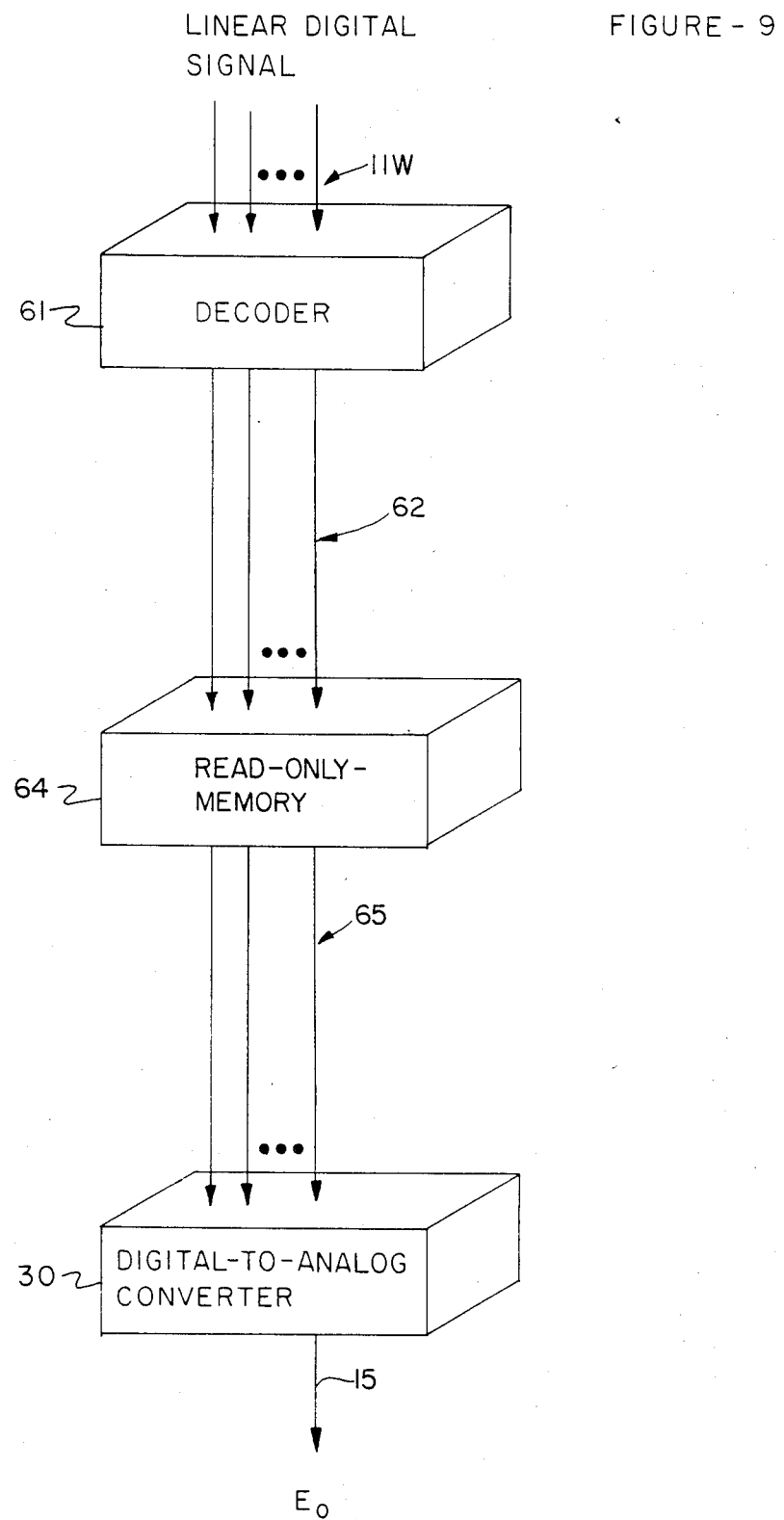
FIG. 9 illustrates a fourth embodiment of the circuit voltage computer, in which a read-only memory and digital-to-analog converter are used.

FIGS. 6–8 illustrate embodiments of circuit voltage computer 14 which are based upon analog voltage circuitry. Referring to FIG. 9, a digital circuit embodiment of circuit voltage computer 14 is depicted, wherein the conversion of the digital signal received from position counter memory 10 via wires 11W (see FIG. 3) to non-linear output voltage $E_o$ transmitted back to bridge network 1 via conductor 15 (see FIG. 1) is accomplished by means of a read-only memory (ROM) and a digital-to-analog converter. Operation of the circuit is as follows:

The digital signal received from position counter memory 10 is input to address decoder 61. Decoder 61 translates the incoming digital signal into a memory address which is transmitted by conductors 62 to ROM 64. ROM 64 then fetches the digital value stored in the corresponding memory location and provides the same as an output to conductors 65. The layout of read-only memory 64 would be similar to the example shown below.

TABLE 6

| Address | $E_o$ Voltage Value |
|---------|---------------------|
| 890     | 2.034               |
| 891     | 2.038               |
| 892     | 2.043               |
| 893     | 2.051               |

To provide a unique $E_o$ voltage value for each of 40 subdivisions on meter dial arcuate scale 83 (FIG. 1) at a maximum sensitivity gain setting over the subject resistance range of 1K ohms to approximately 1 megohms requires about 4100 unique digital voltage values, or roughly a 20K byte ROM chip. When fetched from ROM 64, the digital non-linear $E_o$ voltage value is input to digital-to-analog converter 30 via conductors 65. Converter 30 operates as shown hereinabove to translate the digital representation of the $E_o$ voltage into an analog output voltage, and transmits the corresponding non-linear $E_o$ voltage signal back to bridge network 1 via conductor 15. Since this approach utilizes memory components, it is a relatively expensive approach. However, in applications of the instrument which require the highest possible degree of measurement precision, the digital circuit voltage computer 14 embodiment shown in FIG. 9 can provide unmatched accuracy. Moreover, the continuing price reductions projected for memory products will tend to increase the cost effectiveness of this approach over time.

Figure 10:
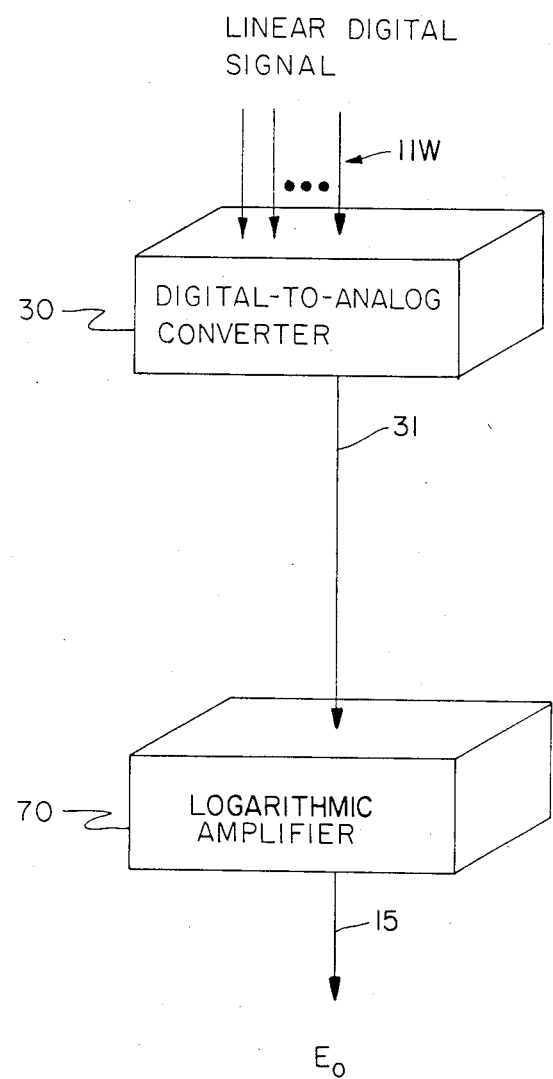
FIG. 10 illustrates a fifth embodiment of the circuit voltage computer using a logarithmic amplifier.

In certain applications of the device it may be acceptable for the instrument to provide a logarithmic response in the measurement of resistance instead of the particular non-linear response curve shown above in Table 3. FIG. 10 shows an embodiment of circuit voltage computer 14 which would perform suitably in such instances. Referring to FIG. 10, the digital signal received from position counter memory 10 is input to digital-to-analog converter 30, which converts it to a linear analog voltage signal. This linear analog voltage is coupled by conductor 31 to the input of logarithmic amplifier 70, which has logarithmic response characteristics over the device's given voltage ranges, such as the National Semiconductor LH0094 log amp. The resuling non-linear analog voltage signal $E_o$, which is also logarithmic in this case, is then applied to bridge network 1 via conductor 15. In this particular case, the non-linear analog voltage signal $E_o$ would appear linear when plotted on a logarithmic scale, although it would still appear as a non-linear curve when plotted on a linear scale.

Figure 11:
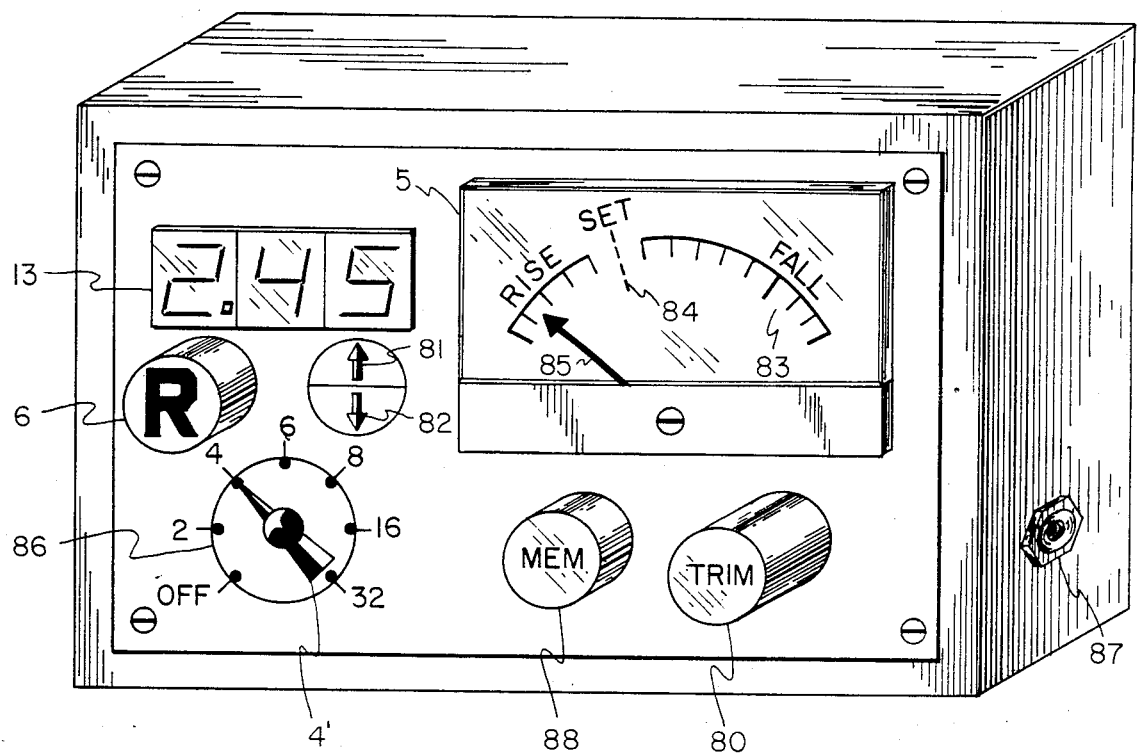
FIG. 11 is a front view of the device shown in FIG. 1 and illustrates a front panel of a housing in which the device is contained.

Referring to FIG. 11, the operator panel for a physical embodiment of the device is depicted. Indicating meter 5 is a moving coil meter having arcuate scale 83 divided into sections. At about one-third scale deflection, there is provided a small sector 84 of the arc marked "SET". the area of the scale to the right of the "SET" position is marked "FALL" and the area to the left of the "SET" position is marked "RISE". Deflections on indicating meter 5 are registered by meter needle 85. Three-digit readout panel 13 is provided for displaying a numeric representation of the subject's resistance. It is typically comprised of three seven-segment light emitting diode displays, and will display numerical tone arm values ranging from '1.00' to '6.00'. The hundredths decimal place will appear only as a zero or a five since that is the maximum level of accuracy which is required.

Automatic resetting indicator lights 81 and 82 are illuminated to alert the operator whenever motion in meter needle 85 is resulting from automatic meter readjustment taking place in the device instead of from changes in the subject's resistance. Manual reset button 6, described above in regard to FIG. 3, is a momentary contact switch which allows the operator to initiate a meter readjustment to reset meter needle 85 to "SET" position 84. This feature is included to provide manual override because occasionally the operator will have a need to adjust meter need 85 to "SET" position 84 at a specific point in time.

Sensitivity control knob 4', described above in regard to FIG. 2, is a combined on/off switch and multi-position resistor switch to control the sensitivity of the device to changes in resistance. Sensitivity scale 86 is marked off in equidistant positions to show the amount of sensitivity amplification. Memory display button 88 is provided to display the contents of total changes counter 9 on digital readout panel 13. The format of this display is rounded to the nearest integer up to a maximum of 999. Turning off the device clears the total changes counter memory. Trim knob 80 controls variable resistor R23 (see FIG. 2) to allow for manual calibration of the device. Jack plug 87 provides means for connecting electrodes 2A and 2B (see FIG. 2) to the bridge network circuit inside the instrument.

Although specific embodiments of the invention have been disclosed herein in detail, it is to be understood that this is for the purpose of illustrating the invention, and should not be construed as necessarily limiting the scope of the invention, since it is apparent that many changes can be made to the disclosed structures by those skilled in the art to suit particular applications.

We claim:
1. An electrical resistance measuring device for measuring and displaying the resistance of a body and changes in resistance thereof, said device comprising in combination:
   (a) a bridge network including:
      i. a voltage control node;
      ii. a first resistance arm having first and second ends, the first end thereof being coupled to a source of ground voltage;
      iii. a second resistance arm having first and second ends, the first end of said second resistance arm being coupled to the second end of said first resistance arm at a junction, and the second end of said second resistance arm being coupled to said voltage control node; and
      iv. first and second terminals for coupling said body across one of said first and second resistance arms;
   (b) amplifier means having an input coupled to one of said first and second terminals for sensing a bridge output voltage thereat, said amplifier means including an output terminal for providing a first output voltage related to said bridge output voltage;
   (c) a meter coupled to said output terminal of said amplifier means and responsive to said first output voltage for indicating changes in the resistance of said body, said meter being adapted to display a range of values extending between maximum and minimum predetermined values;
   (d) a meter registration controller having an input coupled to said output terminal of said amplifier means for receiving said first output voltage, said meter registration controller including detection means for detecting whether said first output voltage is above a first magnitude corresponding to the maximum value displayed by said meter or below a second magnitude corresponding to the minimum value displayed by said meter and generating increment and decrement signals, respectively, in response thereto, said meter registration controller including an oscillator for providing clock signals;
   (e) counter means for storing a digital signal representative of the relative magnitude of the resistance of said body, said counter means being coupled to said detection means and to said oscillator and being responsive to said increment and decrement signals and said clock signals for incrementing or decrementing said digital signal in response thereto, said counter means including a plurality of output terminals for providing said digital signal; and
   (f) non-linear conversion means having a plurality of input terminals coupled to said plurality of output terminals of said counter means for receiving said digital signal, said conversion means producing an analog output voltage as a non-linear function of said digital signal, said non-linear conversion means including an output terminal coupled to said voltage control node of said bridge network for supplying said analog voltage thereto.

2. A device as recited by claim 1 wherein said bridge network also includes a variable resistor having a first end coupled to said junction and a second end coupled to the input of said amplifier means, said variable resistor coupling one of said first and second terminals to said junction, said variable resistor serving to allow for manual calibration of said device when a known resistance value is connected across said first and second terminals in substitution for said body.

3. A device as recited by claim 1 wherein said amplifier means includes:
   (a) a first amplifier having a high impedance input terminal and having an output terminal, the input terminal thereof receiving the bridge output voltage, and the output terminal thereof providing a low impedance source of said bridge output voltage;

(b) a source of an offset voltage, said offset voltage having a magnitude corresponding to a nominal value of the bridge output voltage; and (c) a second amplifier having first and second input terminals and an output terminal, the first input terminal thereof being coupled to the output terminal of said first amplifier and the second input terminal thereof being coupled to said source of the offset voltage, and the output terminal thereof providing an output offset signal corresponding to said bridge output voltage offset by the offset voltage.

4. A device as recited by claim 3 wherein said amplifier means further includes a variable gain amplifier having an input terminal coupled to the output terminal of said second amplifier for receiving the output offset signal therefrom, said variable gain amplifier having an output terminal coupled to the output terminal of said amplifier means for providing the first output voltage signal thereto, said variable gain amplifier including a user-operated selector for selecting the relative gain of said variable gain amplifier, allowing a user to adjust the magnitude of changes indicated by said meter for given changes in the resistance of said body.

5. A device as recited by claim 1 wherein said detection means of said meter registration controller includes:

(a) a first comparator coupled to the input of said meter registration controller and responsive to said first output voltage for selectively generating the increment signal when said first output voltage exceeds said first magnitude; and (b) a second comparator coupled to the input of said meter registration controller and responsive to said first output voltage for selectively generating the decrement signal when said first output voltage falls below said second magnitude.

6. A device as recited by claim 5 wherein said detection means includes a third comparator coupled to the input of said meter registration controller and responsive to said first output voltage for generating an up-/down signal indicative of whether said first output voltage is greater than or less than a nominal voltage magnitude, the nominal voltage magnitude being between said first and second magnitudes, and wherein said counter means is responsive to said up/down signal for determining whether said digital signal is to be incremented or decremented.

7. A device as recited by claim 6 wherein said counter means includes an enable input for enabling or disabling the incrementing and decrementing thereof, and wherein said meter registration controller includes a first flip-flop having an input coupled to said first comparator for being set to a first logic state by the increment signal generated thereby and a second flip-flop having an input coupled to said second comparator for being set to a first logic state by the decrement signal generated thereby, each of said first and second flip-flops including an output terminal for providing an output signal indicating the logic state of each respective flip-flop, said meter registration controller including logic means coupled to said enable input of said counter means and coupled to the output terminals of said first and second flip-flops and responsive to the first logic state of either said first or said second flip-flop for selectively enabling the incrementing and decrementing of said counter means, said first and second flip-flops each including a clear input coupled to said third comparator and responsive to a change in said up/down signal for causing said first and second flip-flops to be reset to a second logic state opposite to said first logic state, said logic means being responsive to said second logic states for selectively disabling the incrementing and decrementing of said counter means.

8. A device as recited by claim 1 wherein said non-linear conversion means includes:

(a) a digital-to-analog converter having inputs coupled to the plurality of output terminals of said counter means for receiving said digital signal therefrom, said digital-to-analog converter having an output terminal for providing a voltage linearly related to said digital signal; and (b) non-linear circuit means coupled to the output terminal of said digital-to-analog converter and responsive to said linearly related voltage for producing said analog output voltage as a non-linear function of said linearly related voltage.

9. A device as recited by claim 1 wherein said non-linear conversion means includes:

(a) an addressable memory having addressing circuitry coupled to the plurality of output terminals of said counter means and responsive to the digital signal received therefrom for selecting one of a plurality of storage locations within said addressable memory, said addressable memory including a plurality of output terminals for providing a digital signal stored at the selected one of said storage locations and (b) a digital-to-analog converter for converting the digital signal provided by said addressable memory into said analog output voltage.

10. A device as recited by claim 1 further comprising:

(a) a digital display controller including:

i. a first counter coupled to said detection means and to said oscillator and responsive to said increment and decrement signals and to said clock signals for storing a digital count ranging from a maximum negative count to a maximum positive count, said maximum negative count and said maximum positive count being of equal magnitude, said first counter selectively incrementing or decrementing the digital count as determined by said increment and decrement signals and said clock signals, said first counter resetting said digital count to zero and generating a display clock signal each time said first counter is incremented beyond said maximum positive count, said first counter resetting said digital count to zero and generating the display clock signal each time said first counter decrements said digital count beyond said maximum negative count; and ii. a second counter for storing a digital value corresponding to a tone arm display value, said second counter having an input terminal coupled to said first counter for receiving said display clock signal and being responsive to said increment and decrement signals for incrementing or decrementing said digital value stored therein, said second counter including a plurality of output terminals for providing said digital value; and (b) a digital display coupled to said plurality of output terminals of said second counter and responsive to said digital value provided thereby for displaying a digital representation of said tone arm display value.

* * * * *